United States Patent
Kim

(10) Patent No.: US 10,493,200 B2
(45) Date of Patent: Dec. 3, 2019

(54) MEDICAL FLUID INJECTOR AND MEDICAL FLUID SUPPLY DEVICE INCLUDING SAME

(71) Applicant: E-WHA MEDITECH INC., Gyeonggi-do (KR)

(72) Inventor: Young Mu Kim, Gyeonggi-do (KR)

(73) Assignee: E-WHA MEDITECH INC., Gyeonggi-Do (KR)

( * ) Notice: Subject to any disclaimer, the term of this patent is extended or adjusted under 35 U.S.C. 154(b) by 19 days.

(21) Appl. No.: 15/552,889

(22) PCT Filed: Feb. 25, 2016

(86) PCT No.: PCT/KR2016/001857
§ 371 (c)(1),
(2) Date: Aug. 23, 2017

(87) PCT Pub. No.: WO2016/137247
PCT Pub. Date: Sep. 1, 2016

(65) Prior Publication Data
US 2018/0028744 A1 Feb. 1, 2018

(30) Foreign Application Priority Data
Feb. 27, 2015 (KR) .................. 10-2015-0028384

(51) Int. Cl.
*A61M 5/148* (2006.01)
*A61M 5/142* (2006.01)
(Continued)

(52) U.S. Cl.
CPC ............ *A61M 5/148* (2013.01); *A61M 5/142* (2013.01); *A61M 5/145* (2013.01);
(Continued)

(58) Field of Classification Search
CPC ...... A61M 5/148; A61M 5/142; A61M 5/145; A61M 5/14526; A61M 5/1618;
(Continued)

(56) References Cited

U.S. PATENT DOCUMENTS 3,727,614 A * 4/1973 Kniazuk ............... A61M 5/204
604/115
4,627,839 A * 12/1986 Young .................. A61M 5/142
128/DIG. 12

(Continued)

FOREIGN PATENT DOCUMENTS

| JP | 2006-021055 | 1/2006 |
| JP | 2011-510738 | 4/2011 |

(Continued)

*Primary Examiner* — Nathan R Price
*Assistant Examiner* — Mark Alan Igel
(74) *Attorney, Agent, or Firm* — Clark Hill PLC; James R. Foley

(57) ABSTRACT

A medical fluid injector is connected to a supply tube through which medical fluid is supplied and a discharge tube through which the medical fluid is discharged. The medical fluid injector has a housing body and a reservoir module which is disposed within the housing body. The housing body has a grip portion, which has a length in the longitudinal direction that is greater than a width in a direction orthogonal to the longitudinal direction, and a pair of button protection arms located at one end adjacent to the grip portion. The reservoir module has a reservoir bag, which stores and discharges the medical fluid, and a push button which pushes the reservoir bag to discharge the medical fluid in the reservoir bag. The reservoir bag is fluidically connected to the supply tube and the discharge tube. A portion of the push button is positioned between the button protection arms.

18 Claims, 24 Drawing Sheets

(51) Int. Cl.
*A61M 5/145* (2006.01)
*A61M 5/168* (2006.01)
*A61M 5/14* (2006.01)

(52) U.S. Cl.
CPC .... *A61M 5/14526* (2013.01); *A61M 5/16818* (2013.01); *A61M 2005/1405* (2013.01); *A61M 2005/14506* (2013.01); *A61M 2202/04* (2013.01)

(58) Field of Classification Search
CPC ........... A61M 2005/1405; A61M 2005/14506; A61M 2202/04; G05B 2219/39447; H01H 2300/026; F41A 17/54
See application file for complete search history.

(56) References Cited

U.S. PATENT DOCUMENTS

| | | | | |
|---|---|---|---|---|
| 5,009,641 | A * | 4/1991 | Gorton | A61M 5/142 604/131 |
| 5,011,477 | A * | 4/1991 | Winchell | A61M 5/1424 128/DIG. 12 |
| 5,061,243 | A * | 10/1991 | Winchell | A61M 5/1424 604/132 |
| 5,069,668 | A * | 12/1991 | Boydman | A61M 5/172 604/121 |
| 5,135,491 | A * | 8/1992 | Baldwin | A61M 5/141 604/135 |
| 5,755,692 | A * | 5/1998 | Manicom | A61M 5/1456 604/152 |
| 5,891,102 | A * | 4/1999 | Hiejima | A61M 5/1424 604/185 |
| 5,957,895 | A | 9/1999 | Sage et al. | |
| 6,074,369 | A | 6/2000 | Sage et al. | |
| 7,475,797 | B2 * | 1/2009 | Kim | A61M 5/14526 222/387 |
| 7,905,865 | B2 | 3/2011 | Lee | |
| 8,512,284 | B2 * | 8/2013 | Lee | A61M 5/152 604/131 |
| 8,548,623 | B2 * | 10/2013 | Poutiatine | A61J 7/0053 700/236 |
| 9,492,615 | B1 * | 11/2016 | Barnard | A61M 5/16804 |
| 9,526,832 | B1 * | 12/2016 | Barnard | A61M 5/172 |
| 9,572,931 | B2 * | 2/2017 | Shay | A61M 5/16804 |
| 9,919,101 | B1 * | 3/2018 | Barnard | A61M 5/16804 |
| 2004/0127860 | A1 * | 7/2004 | Rake | A61M 5/14216 604/246 |
| 2005/0033223 | A1 * | 2/2005 | Herrera | A61M 5/142 604/67 |
| 2005/0177096 | A1 * | 8/2005 | Bollish | A61B 5/02055 604/65 |
| 2008/0142554 | A1 * | 6/2008 | Lafferty | A61M 5/001 222/566 |
| 2008/0161753 | A1 * | 7/2008 | Gillespie | A61M 5/142 604/65 |
| 2009/0143733 | A1 * | 6/2009 | Keenan | A61M 5/142 604/151 |
| 2010/0249763 | A1 * | 9/2010 | Larson | A61B 18/22 606/8 |
| 2011/0108160 | A1 | 5/2011 | Lee | |
| 2012/0157918 | A1 * | 6/2012 | Valle | A61M 5/14216 604/151 |
| 2013/0023820 | A1 * | 1/2013 | Solomon | A61M 5/1452 604/66 |
| 2016/0074575 | A1 * | 3/2016 | Hyun | A61M 5/14216 604/152 |
| 2017/0106137 | A1 * | 4/2017 | Lee | A61M 5/1452 |
| 2018/0317841 | A1 * | 11/2018 | Novak, Jr. | A61B 5/4839 |

FOREIGN PATENT DOCUMENTS

| | | |
|---|---|---|
| JP | 2013-081598 A | 5/2013 |
| JP | 2014-502525 A | 2/2014 |
| KR | 10-2005-0099951 | 10/2005 |
| KR | 20-2009-0008046 | 8/2009 |
| KR | 10-2010-0035350 | 4/2010 |
| KR | 10-1028847 | 4/2011 |
| KR | 10-1127128 | 3/2012 |
| WO | 03/066138 | 8/2003 |
| WO | 2012/080862 A2 | 6/2012 |

* cited by examiner

MEDICAL FLUID INJECTOR AND MEDICAL FLUID SUPPLY DEVICE INCLUDING SAME

TECHNICAL FIELD

The present disclosure relates to a medical fluid injector which is positioned at a supply path of medical fluid and temporarily stores and discharges the medical fluid, and a medical fluid supply device including the medical fluid injector.

BACKGROUND

A device, which supplies a patient with medical fluid such as an analgesic medicine at a uniform amount per hour, has been used in the art. Such a medical fluid supply device has a medical fluid chamber which stores the medical fluid, and a medical fluid tube which allows the medical fluid discharged from the medical fluid chamber to flow to an injection needle or a catheter inserted into the body of a patient.

Further, a medical fluid supply device equipped with a medical fluid injector, which is held in the hand of a patient and can be operated by the patient for patient-controlled analgesia, has been used in the art. Such a medical fluid injector is connected to the medical fluid tube of the medical fluid supply device and temporarily stores a predetermined amount of the medical fluid. As the patient manipulates the medical fluid injector by himself, the medical fluid stored in the medical fluid injector is supplied to the patient together with the medical fluid supplied by the medical fluid supply device, and thus can temporarily increase the amount of the medical fluid supplied to the patient. For example, International Application Publication No. WO 03/066138 A1 discloses an example of a medical fluid supply device which supplies medical fluid by means of pressure of a gas, and an example of a medical fluid injector.

An example of a medical fluid injector of prior art is shown in FIG. 1. Referring to FIG. 1, the medical fluid injector 10 of the prior art has a housing body 11 and a push button 12, which is exposed on a flat upper surface of the housing body 11 and can be pushed by a patient. Further, the medical fluid injector 10 has a reservoir bag (not shown), which temporarily stores medical fluid, below the push button 10 within the housing body 11. The medical fluid from a medical fluid chamber of a medical fluid supply device is stored in the reservoir bag through a tube 13A. If the reservoir bag discharges the medical fluid, which is stored in the reservoir bag, in response to pressing applied by the push button 12, the discharged medical fluid is injected to the patient through a tube 13B.

As illustrated in FIG. 1, the housing body 11 of the medical fluid injector 10 of the prior art has a flattened shape, and the push button 12 is exposed on the flat upper surface of the housing body 11. Thus, it is easy for the push button 12 to be pressed carelessly and unintendedly. Because the medical fluid injector 10 discharges the medical fluid upon pressing of the push button, the unintended pressing of the push button 12 leads to an unnecessary injection of the medical fluid.

Since an injection needle for injecting medical fluid is inserted into one arm of the patient, the patient generally operates the medical fluid injector 10 by using the hand of the other arm. In such a case, as illustrated in FIG. 1, the patient puts the flattened housing body 11 of the medical fluid injector 10 on the palm and pushes the push button 12 with the thumb. However, it is not easy for the patient to operate the medical fluid injector 10, which includes the flattened housing body 11 and the push button 12 located on the upper surface of the housing body, with only one hand. And in the state where the patient grips the flattened housing body 11, the patient cannot easily push the push button 12 located on the upper surface of the housing body 11 with his thumb. As such, the medical fluid injector 10 of the prior art fails to provide satisfactory user convenience.

SUMMARY

Embodiments disclosed in the present disclosure solve the aforementioned problems of the prior art. Embodiments of the present disclosure provide a medical fluid injector that prevents a push button from being pushed unintendedly and improves user convenience. Further, embodiments of the present disclosure provide a medical fluid injector that has the aforementioned functions and can be easily assembled by modularized internal parts.

One aspect of the present disclosure provides a medical fluid injector which is connected to a supply tube through which medical fluid is supplied and a discharge tube through which the medical fluid is discharged, and which is configured to store and discharge the medical fluid. The medical fluid injector according to one embodiment includes a housing body, which forms an outer body of the medical fluid injector, and a reservoir module which is fixed inside the housing body and stores and discharges the medical fluid. The housing body has a central axis extending in a longitudinal direction. The housing body includes: a grip portion which forms a portion of an outer peripheral surface of the housing body and a length of which in the longitudinal direction is greater than a width of the grip portion in a direction orthogonal to the longitudinal direction; and a pair of button protection arms located at one end of the housing body adjacent to the grip portion. The reservoir module is fixed to the housing body within the housing body, and includes a reservoir bag and a push button. The reservoir bag is fluidically connected to the supply tube and the discharge tube and stores the medical fluid. The push button pushes the reservoir bag to discharge the medical fluid in the reservoir bag. The push button is partially positioned between the button protection arms, and is movable along the central axis of the housing body.

In one embodiment, the reservoir bag includes an inlet tube fluidically connected to the supply tube and an outlet tube fluidically connected to the discharge tube. The reservoir module further includes: a reservoir housing configured to house the reservoir bag and to support the push button such that the push button is movable along the central axis; and a locker configured to open and block one of the inlet tube and the outlet tube of the reservoir bag along with a movement of the push button.

In such an embodiment, the locker includes: a locking lever rotatably coupled to the reservoir housing and configured to press the one of the inlet tube and the outlet tube; and a locker spring configured to bias the locking lever such that the locking lever presses the one of the inlet tube and the outlet tube. Further, the push button includes a drive arm for rotating the locking lever, and the reservoir housing includes a guide slot to which the drive arm is slidably fitted and which extends in parallel with the central axis. The locking lever includes a driven arm in contact with the drive arm and a pressing arm pressing the one of the inlet tube and the outlet tube. The locker spring biases the locking lever in a direction opposite to a direction in which the driven arm is rotated by the drive arm. Further, a portion of the driven arm in contact with at least a side portion of the drive arm includes an inclined surface, and the inclined surface is inclined with respect to the central axis.

In one embodiment, the reservoir housing includes: a bottom portion on which the reservoir bag is placed; a side wall extending along an edge of the bottom portion; and an insertion slot formed adjacent to the bottom portion to penetrate through the side wall. The reservoir bag is inserted inside of the reservoir housing through the insertion slot. In such an embodiment, the reservoir module further includes a support plate disposed between the bottom portion of the reservoir housing and a lower surface of the reservoir bag. Further, in such an embodiment, at an inner surface of the housing body, the housing body includes: a support rib supporting a lower surface of the bottom portion of the reservoir housing; an engagement rib in contact with an upper end of the side wall of the reservoir housing; and an insertion rib inserted into the insertion slot of the reservoir housing.

In one embodiment, the reservoir housing includes a button stopper restricting a movement of the push button toward the button protection arms. The button stopper is elastically deformable toward inside and outside of the reservoir housing.

In one embodiment, the reservoir module further includes a pressing plate, which is disposed between the reservoir bag and the push button and presses the reservoir bag by pushing of the push button. The pressing plate includes a cushion member in surface-contact with a portion of an upper surface of the reservoir bag. In such an embodiment, the push button includes a button spring, which is disposed between a lower surface of the push button and the pressing plate and biases the push button toward the button protection arms. Further, the medical fluid injector of such an embodiment further includes a cotter which is removably fixed between the button protections arms and the push button. The push button is pushed by the cotter to contract the reservoir bag to a minimum in the direction of the central axis. As a further example, the cotter is removably fitted to the button protection arms such that the push button is pushed.

In one embodiment, the medical fluid injector further includes a capillary tube module fixed adjacent to the reservoir module within the housing body. The capillary tube module includes: a first capillary tube; a first medical fluid flow path through which the medical fluid is supplied from the supply tube via the first capillary tube to the reservoir bag; a second capillary tube; and a second medical fluid flow path through which the medical fluid flows from the supply tube via the second capillary tube to the discharge tube and through which the medical fluid stored in the reservoir bag is supplied.

In one embodiment, the pair of the button protection arms of the housing body are integrally formed. Further, the pair of the button protection arms may form an annular shape.

In one embodiment, the housing body includes a first housing, which comprises a half portion of the housing body with respect to the central axis, and a second housing, which comprises another half portion of the housing body with respect to the central axis. The first housing includes a pair of tube fixing protrusions at a lower edge. The second housing includes, at a lower edge, a pair of tube fixing recesses to which the tube fixing protrusions are inserted respectively and which are deeper than protrusion lengths of the tube fixing protrusions.

In one embodiment, a cross sectional shape of the grip portion of the housing body includes any one of a circle, an ellipse and a polygon of at least a triangle.

Another aspect of the present disclosure provides a medical fluid supply device which supplies a patient with medical fluid. The medical fluid supply device according to one embodiment includes: a chamber assembly having a medical fluid chamber configured to store the medical fluid; a tube assembly connecting the medical fluid chamber and a user; and the medical fluid injector of one of the aforementioned embodiments. The tube assembly includes the supply tube through which the medical fluid is supplied from the medical fluid chamber to the medical fluid injector and the discharge tube through which the medical fluid is discharged from the medical fluid injector. The reservoir bag of the medical fluid injector is fluidically connected to the supply tube and the discharge tube.

In the medical fluid injector according to the embodiments, a pair of the button protection arms are provided at one end of the elongated housing body, the push button is disposed between the button protection arms, and the push button can be pushed only in the longitudinal direction of the housing body. Thus, the medical fluid injector according to the embodiments can prevent the push button from being pushed carelessly and unintendedly. Further, the housing body has the grip portion having a shape of an elongated cylinder or an elongated polygonal cylinder and the push button is located at an end of the grip portion in the longitudinal direction. Thus, the user can conveniently grip the medical fluid injector according to the embodiments by means of only one hand and can easily push the push button. Further, the medical fluid injector according to the embodiment includes the reservoir module into which the parts for storage and discharge of the medical fluid are assembled, and the capillary tube module into which the parts for providing the flow path of the medical fluid within the medical fluid injector are assembled, thus achieving easy assembly.

DETAILED DESCRIPTION

Figure 1:
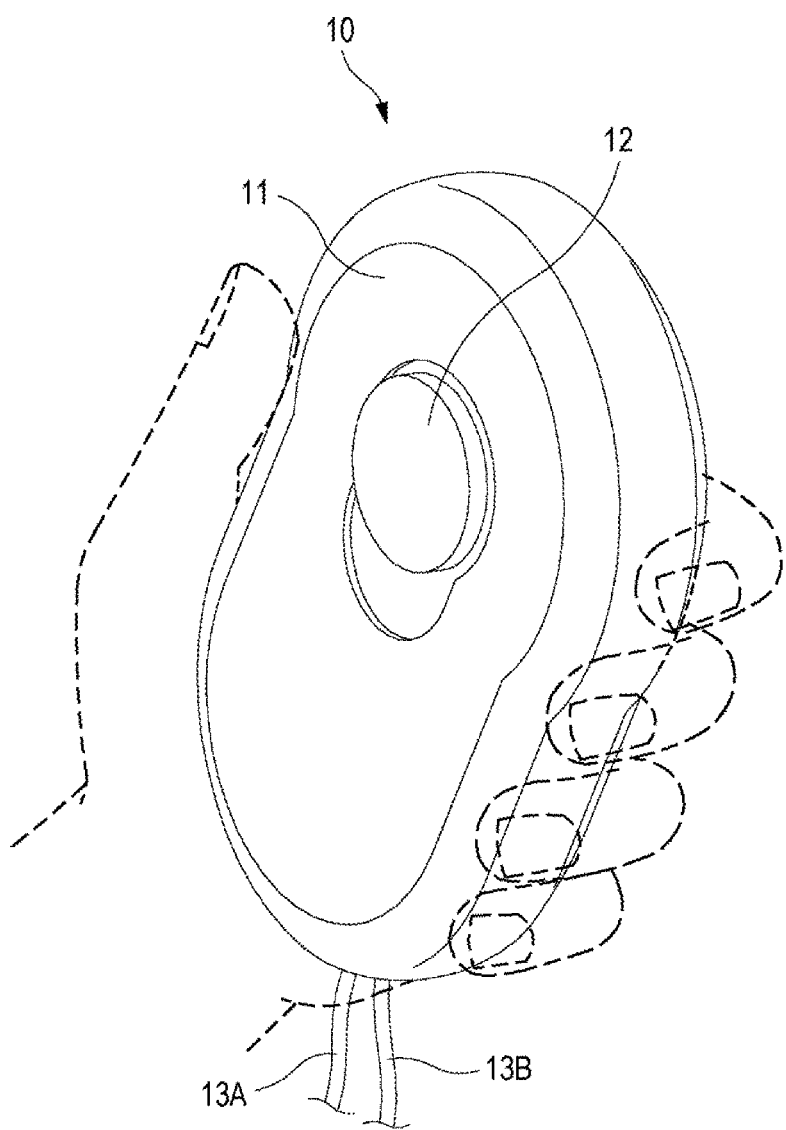
FIG. 1 is an example of a prior art medical fluid injector and shows an example where a user uses the prior art medical fluid injector.

Descriptions are made as to embodiments of a medical fluid injector and a medical fluid supply device according to the present disclosure with reference to the accompanying drawings. In the drawings, like reference numerals denote like or corresponding elements or parts.

The directional term "upward," "upper," or the like as used herein means a direction in which a push button is located in a medical fluid injector, while the directional term "downward," "lower," or the like means a direction opposite to the upward or upper direction. The medical fluid injector shown in the accompanying drawings may be oriented differently and the aforementioned directional terms may be interpreted accordingly. Further, as used herein, the phrase "fluidically connected" means that two parts are connected directly or by means of one or more tubes such that fluid (i.e., medical fluid) can flow between the two parts.

Figure 2:
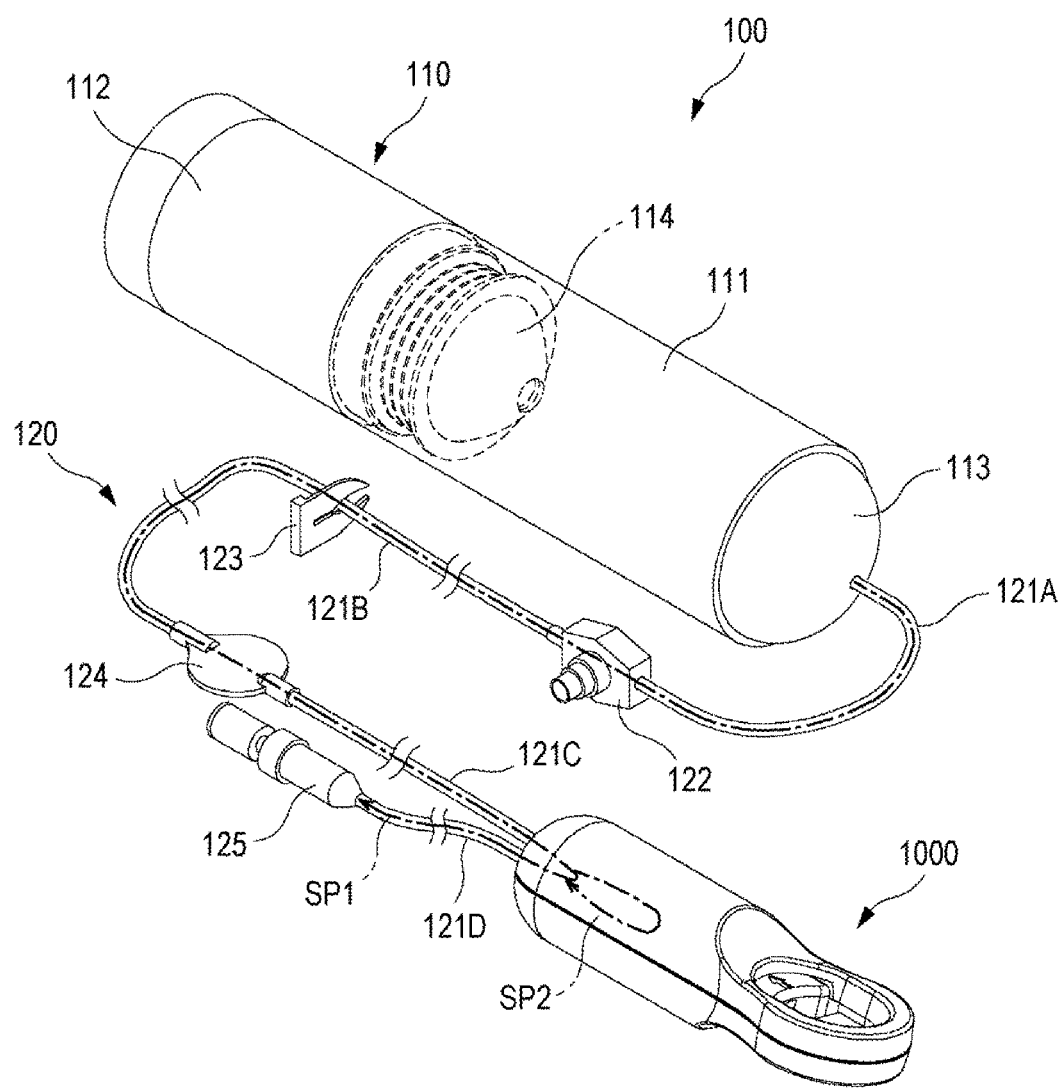
FIG. 2 is a perspective view showing a medical fluid supply device according to one embodiment.

FIG. 2 shows a medical fluid supply device according to one embodiment, which includes a medical fluid injector according to one embodiment. The medical fluid supply device 100 shown in FIG. 2 includes a chamber assembly 110 configured to store medical fluid and discharge the stored medical fluid, a tube assembly 120 for flow of the medical fluid, and a medical fluid injector 1000 according to one embodiment which is connected to the tube assembly 120.

The chamber assembly 110 includes a medical fluid chamber 111 configured to store the medical fluid. The medical fluid chamber 111 may comprise a cylinder provided with a plunger for extruding the medical fluid. Alternatively, the medical fluid chamber may comprise a balloon which stores the medical fluid and is expandable and contractible. In this embodiment, the chamber assembly 110 has the medical fluid chamber 111, a gas generator 112, a plug 113, and a plunger 114. The gas generator 112 is air-tightly coupled to one end of the medical fluid chamber 111. The gas generator 112 is configured to generate carbon dioxide gas at approximately uniform pressure through, for example, a reaction of citric acid and sodium hydrogen carbonate. The plug 113 is air-tightly coupled to an opposite end of the medical fluid chamber 111. The plunger 114 is disposed in front of a nozzle of the gas generator 112 within the medical fluid chamber 111. The pressure of the gas, which is generated by the gas generator 112, propels the plunger 114 toward the plug 113 within the medical fluid chamber 111. The medical fluid is stored within the medical fluid chamber 111 between the plug 113 and the plunger 114. The medical fluid stored in the medical fluid chamber 111 includes, but is not limited to, any analgesic medicine. The chamber assembly 110 of this embodiment propels the plunger 114 toward the plug 113 by the pressure of the gas generated by the gas generator 112. Due to the approximately uniform pressure of the gas generated by the gas generator 112, the plunger 114 is moved at approximately uniform speed, and thus the medical fluid in the medical fluid chamber 111 is supplied at a uniform amount per hour. In another embodiment, the chamber assembly of the medical fluid supply device may have a cylindrical or conical housing and an expandable and contractible balloon which is disposed within such a housing and stores the medical fluid. The chamber assembly of such an embodiment supplies the medical fluid in the balloon by the contraction force of the balloon.

The tube assembly 120 connects the medical fluid chamber 111 of the chamber assembly 110 to a user to whom the medical fluid is to be administered. The tube assembly 120 has a plurality of tubes 121A, 121B, 121C, and 121D. The tubes 121A, 121B, 121C, and 121D are sequentially connected to form a first supply path SP1 of the medical fluid. The tube assembly 120 includes a valve device 122 to which the medical fluid is injected, a clamp 123 clamping the tube 121B to block the supply of the medical fluid, a filter 124 filtering the medical fluid, and a connector 125 which is connected to an injection needle or a catheter inserted into the body of a patient.

Figure 7:
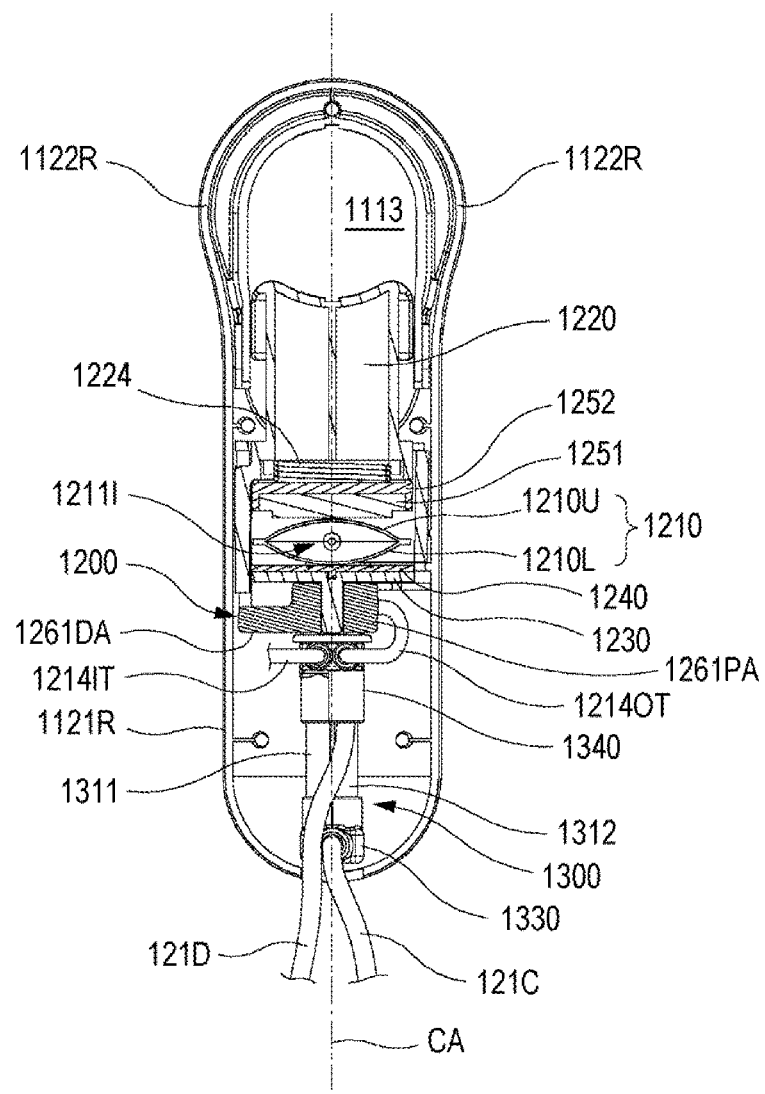
FIG. 7 is a sectional view taken along the line VII-VII of FIG. 6.
Figure 8:
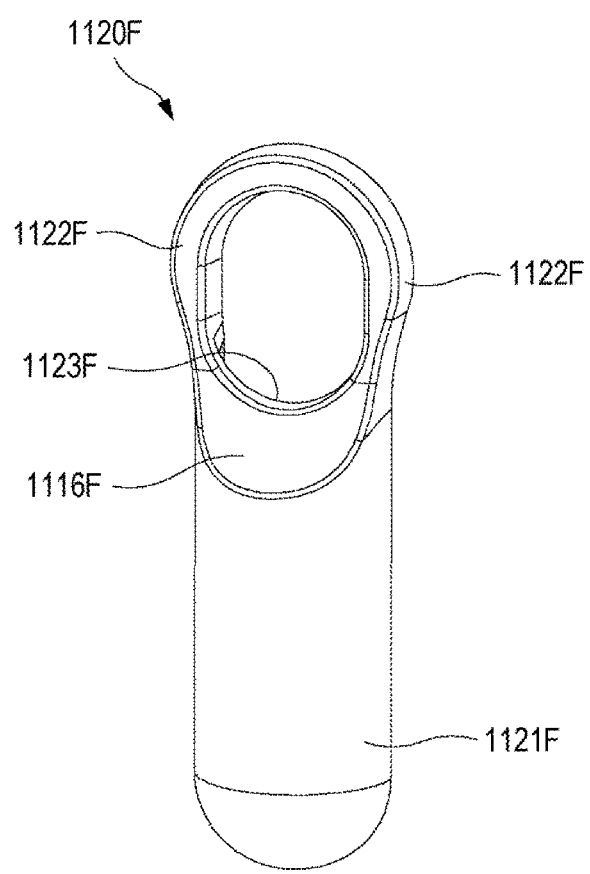
FIG. 8 is a perspective view showing a first housing of the medical fluid injector shown in FIG. 4.
Figure 9:
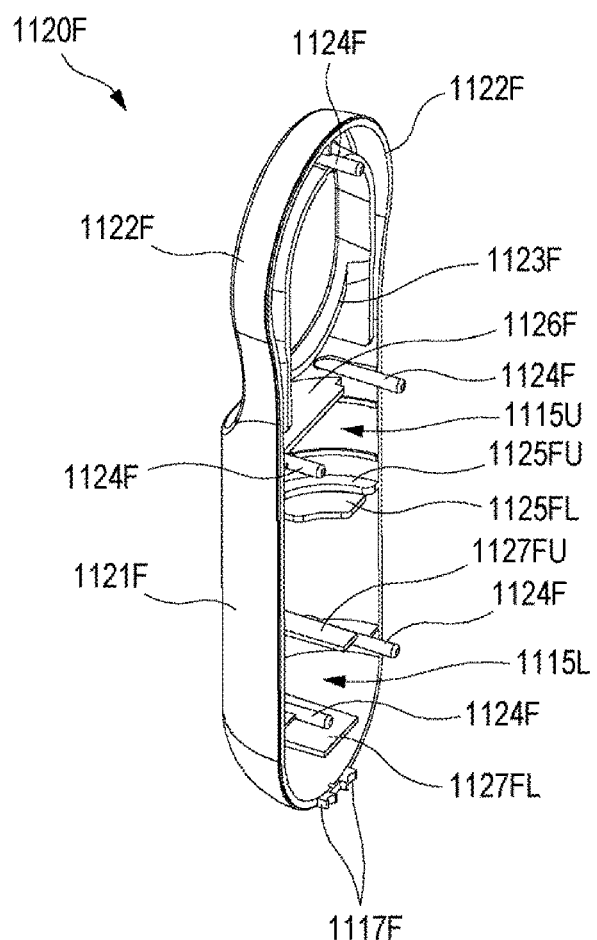
FIG. 9 is a perspective view showing a rear side of the first housing shown in FIG. 8.
Figure 10:
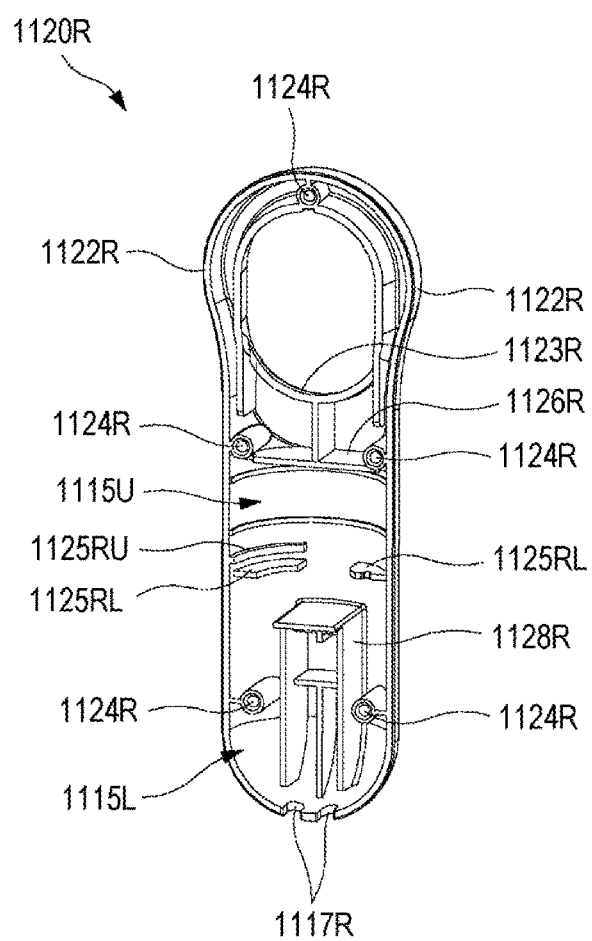
FIG. 10 is a perspective view showing a second housing of the medical fluid injector shown in FIG. 4.
Figure 11:
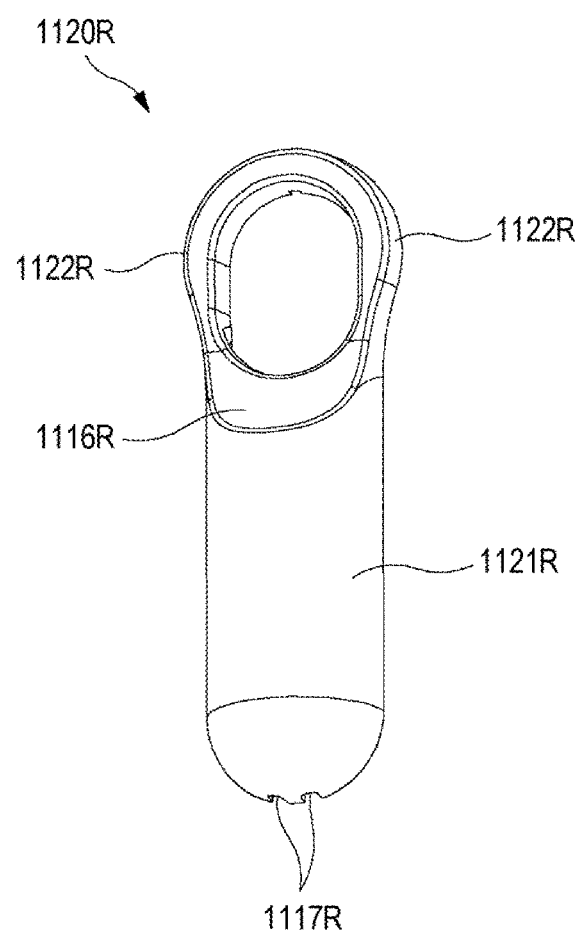
FIG. 11 is a perspective view showing a rear side of the second housing shown in FIG. 10.
Figure 12:
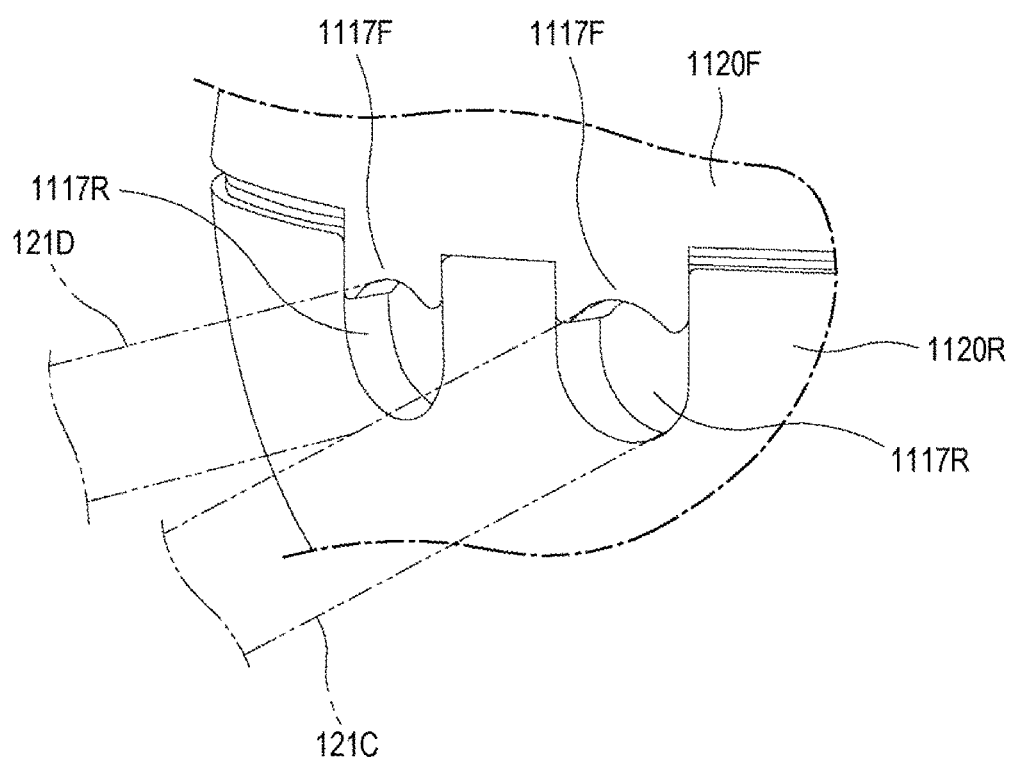
FIG. 12 is a perspective view showing a lower portion of the medical fluid injector shown in FIG. 4.

The medical fluid injector 1000 according to one embodiment is disposed between the filter 124 and the connector 125 of the tube assembly 120. Specifically, the tube assembly 120 includes the supply tube 121C through which the medical fluid is supplied from the medical fluid chamber 111 to the medical fluid injector 1000, and the discharge tube 121D through which the medical fluid is discharged from the medical fluid injector 1000. The medical fluid injector 1000 is connected to the supply tube 121C and the discharge tube 121D to temporarily store the medical fluid supplied from the medical fluid chamber 111 and discharge the medical fluid. The medical fluid discharged from the medical fluid chamber 111 is introduced into the medical fluid injector 1000 through the supply tube 121C, passes through the medical fluid injector 1000, and enters the connector 125 through the discharge tube 121D. The medical fluid injector 1000 has a second supply path SP2 of the medical fluid. The second supply path SP2 branches from the first supply path SP1, which extends from the medical fluid chamber 111 to the connector 125, and reconnects to the first supply path SP1. The medical fluid injector 1000 includes a reservoir bag (see reference number 1210 of FIG. 7), which is positioned at such a branched, second supply path SP2 and temporarily stores the medical fluid. The reservoir bag is fluidically connected to the supply tube 121C and the discharge tube 121D. In the state where the medical fluid of a uniform amount per hour is supplied from the chamber assembly 110 to the user, the user can transiently increase the amount of the medical fluid, which is supplied to the user, by operating the medical fluid injector 1000 when necessary.

FIGS. 3 to 25 show a medical fluid injector of one embodiment, which is employed in the medical fluid supply device, and various parts constituting the medical fluid injector. Descriptions are made as to the medical fluid injector according to one embodiment with reference to FIGS. 3 to 25.

Figure 3:
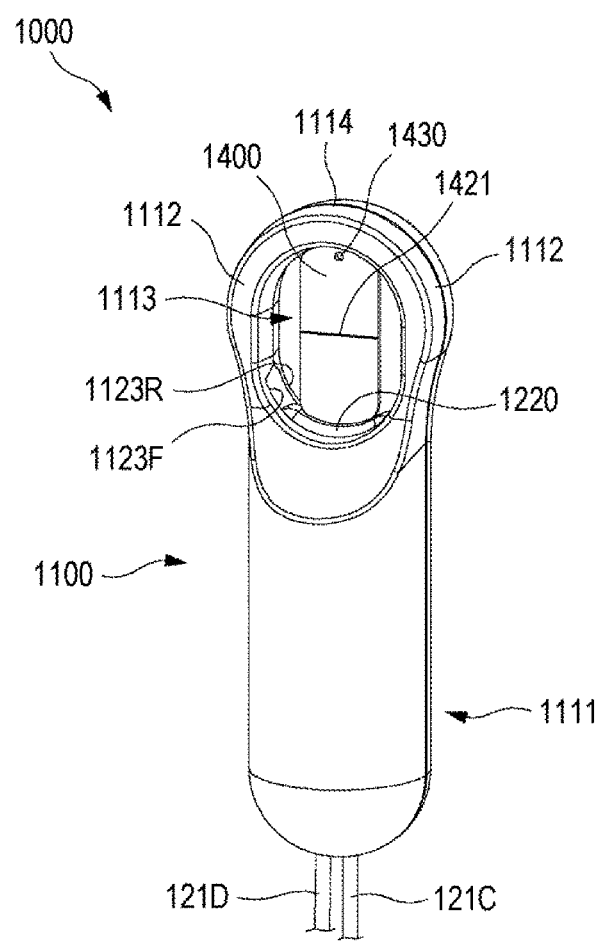
FIG. 3 is a perspective view of a medical fluid injector according to one embodiment, showing the medical fluid injector in an unused state.
Figure 4:
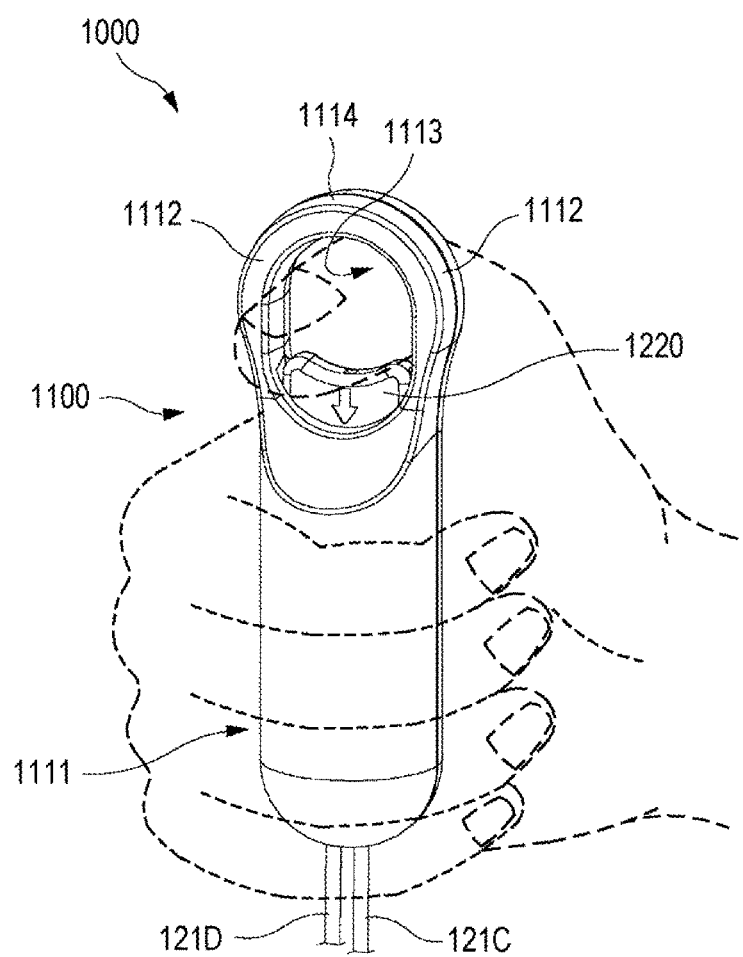
FIG. 4 is a perspective view showing a medical fluid injector with a cotter removed therefrom according to one embodiment, and further shows an example where a user grips the medical fluid injector.
Figure 5:
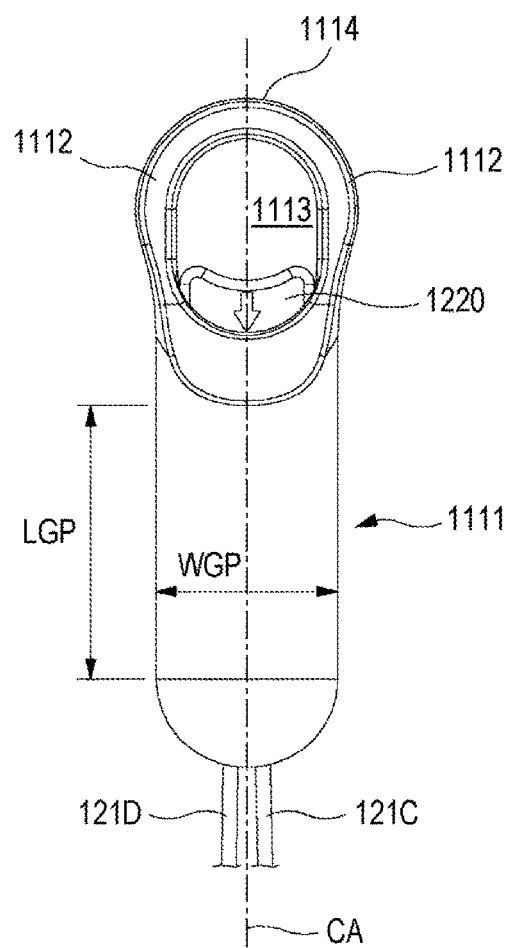
FIG. 5 is a front view of the medical fluid injector shown in FIG. 4.

FIG. 3 shows the medical fluid injector according to one embodiment, which is in an unused state. The medical fluid injector 1000 shown in FIG. 3 is provided together with the medical fluid supply device 100, and is under the state where the inside is not filled with the medical fluid. Further, as shown in FIG. 3, the medical fluid injector 1000, which is not yet filled with the medical fluid, is provided in the state where a push button 1220 is pressed to a maximum by a removable cotter 1400. If the user (e.g., a doctor, nurse, patient, etc.) removes the cotter 1400, then the push button 1220 protrudes and therefore the medical fluid injector 1000 can come to be in a useable state. If the cotter 1400 is removed from the medical fluid injector 1000 which is in an unused state as shown in FIG. 3, the push button 1220 protrudes as shown in FIG. 4 and thus the medical fluid injector 1000 comes to be in the useable state.

Referring to FIGS. 4 to 7, the medical fluid injector 1000 according to one embodiment includes: a housing body 1100 which functions as an outer body of the medical fluid injector, a reservoir module 1200 disposed within the housing body 1100 and fixed to the housing body 1100, and a capillary tube module 1300 disposed below the reservoir module 1200 within the housing body 1100 and fixed to the housing body 1100. The reservoir module 1200 stores and discharges the medical fluid which is supplied from, for example, the medical fluid chamber 111 of the medical fluid supply device 100. The capillary tube module 1300 allows the medical fluid to flow, and divides the flow of the medical fluid.

The housing body 1100 houses and fixes parts for storage and discharge of the medical fluid (i.e., the reservoir module 1200 and the capillary tube module 1300) therein. The housing body 1100 has a size which allows the user to grip the housing body with his or her hand. The housing body 1100 is formed of a transparent or translucent plastic material.

The housing body 1100 has a length that is longer than its width. The housing body 1100 has a central axis CA extending in its longitudinal direction (e.g., a vertical direction in FIG. 5). The housing body 1100 includes a grip portion 1111, which forms a portion of an outer peripheral surface of the housing body 1100 in longitudinal and circumferential directions of the housing body and which the user can grip. In the grip portion 1111 of the housing body 1100, a length LGP of the grip portion 1111 in the longitudinal direction of the housing body 1100 is longer than a width WGP of the housing body 1100 in a direction orthogonal to the longitudinal direction. In this embodiment, the grip portion 1111 has a cylindrical shape with a length longer than its width. Accordingly, when a cross section of the housing body 1100 is taken at the grip portion 1111, the shape of such a cross section includes a circular shape. Further, the housing body 1100 includes, at one end thereof, a pair of button protection arms 1112 which are located adjacent to the grip portion 1111. The button protection arms 1112 extend upwardly from an upper end of the grip portion 1111 along the central axis CA and are curved with a slight curvature. Thus, a hole is defined between the pair of the button protection arms 1112. The hole functions as an insertion opening 1113 into which the user can insert a finger (e.g., a thumb or a forefinger) when using the medical fluid injector 1000. The insertion opening 1113 is perforated in the housing body 1100 in a direction orthogonal to the central axis CA of the housing body 1100. A surface of the grip portion 1111 (i.e., the outer peripheral surface of the housing body 1100 at the grip portion) may include a smooth surface or a surface having a certain surface roughness. Further, in this embodiment, the pair of the button protection arms 1112 of the housing body 1100 are integrally formed. That is, the pair of the button protection arms 1112 have a connection portion 1114 connecting the button protection arms 1112. Inner surfaces of the pair of the button protection arms 1112 face respective side surfaces of the push button 1220, and an inner surface of the connection portion 1114 faces a top surface of the push button 1220. In this embodiment, when the medical fluid injector 1000 is viewed from the front or the rear, the pair of the button protection arms 1112 and the connection portion 1114 form approximately an annular shape.

As shown in FIG. 4, the user can position the grip portion 1111 of the housing body in his or her palm and grip the medical fluid injector 1000 in such a manner that the fingers of the user close around the grip portion 1111. Further, in the state where the user grips the grip portion 1111 of the housing body 1100, the user can insert, for example, the thumb into the insertion opening 1113 of the housing body 1100 and can push the push button 1220. Since the grip portion 1111 of the housing body 1100 has a cylindrical shape, the user can grip the grip portion 1111 without feeling of irritation. Accordingly, the medical fluid injector 1000 according to the embodiments significantly enhances user convenience. Further, since the push button 1220 is protected by the button protection arms 1112 and is manipulated only by the finger inserted into the insertion opening 1113, the medical fluid injector 1000 cannot be operated in a situation that the user does not intend. Accordingly, the medical fluid injector according to the embodiments can prevent an unintended administration of the medical fluid.

The reservoir module 1200 includes at least the reservoir bag 1210 and the push button 1220 for pushing the reservoir bag 1210 in a direction of the central axis CA of the housing body 1100. Further, as in this embodiment, the reservoir module 1200 includes a reservoir housing 1230, which houses the reservoir bag 1210 and supports the push button 1220 to be movable in the direction of the central axis CA of the housing body 1100. The medical fluid is temporarily stored in the reservoir bag 1210. The push button 1220 pushes the reservoir bag 1210 downward, thereby discharging the medical fluid stored in the reservoir bag 1210. The reservoir housing 1230 has a cylindrical shape extending along the central axis CA of the housing body 1100. The push button 1220 is coupled to the reservoir housing 1230 so as to move along the central axis CA of the housing body 1100. When the reservoir module 1200 is coupled to the housing body 1100, a portion of the push button 1220 protrudes through button slots 1123F and 1123R provided at an upper end of the grip portion 1111 of the housing body 1100 and is positioned between the button protection arms 1112. Since the push button 1220 is moved only along the central axis CA of the housing body 1100 due to the reservoir housing 1230, the push button 1220 can only be pushed toward a direction from an upper end of the housing body 1100 to a lower end of the housing body 1100. Further, since the button protection arms 1112 extend from the grip portion 1111 along the central axis CA of the housing body 1100, the push button 1220 can be protected from push or contact in a direction other than the direction from the upper end of the housing body 1100 toward the lower end of the housing body 1100.

The capillary tube module 1300 is located below the reservoir module 1200 within the housing body 1100. The capillary tube module 1300 is connected to the supply tube 121C and the discharge tube 121D of the medical fluid supply device 100. Further, the capillary tube module 1300 is fluidically connected to the reservoir bag 1210. The capillary tube module 1300 has a medical fluid flow path which constitutes a portion of the above-described first supply path SP1 of the medical fluid supply device 100. Further, the capillary tube module 1300 has a medical fluid flow path, which branches from the first supply path SP1 and through which the medical fluid flows to the reservoir bag 1210, and a medical fluid flow path through which the medical fluid is added from the reservoir bag 1210.

The housing body 1100 of the medical fluid injector 1000 according to one embodiment is described in detail with reference to FIGS. 4 to 12.

A pair of half housings, the outer surface shapes of which are approximately symmetrical with respect to the central axis CA, are coupled to each other and constitute the housing body 1100. That is, the housing body 1100 includes a first housing 1120F, which becomes a front half of the housing body 1100 with respect to the central axis CA, and a second housing 1120R, which becomes a rear half of the housing body 1100 with respect to the central axis CA. The first housing 1120F and the second housing 1120R are coupled to each other through fitting. For fitting the first housing 1120F and the second housing 1120R with each other, the first housing 1120F has a plurality of dowels 1124F protruding from an edge of the first housing 1120F, and the second housing 1120R has, at its edge, a plurality of dowel holes 1124R to which the dowels 1124F are fitted.

The first housing 1120F includes a first grip portion 1121F, which corresponds to a front half of the grip portion 1111, and a first button protection arm 1122F, which corresponds to a front half of the button protection arm 1112. Further, the second housing 1120R includes a second grip portion 1121R, which corresponds to a rear half of the grip portion 1111, and a second button protection arm 1122R, which corresponds to a rear half of the button protection arm 1112. An arcuate button slot 1123F is formed at an upper end of the first grip portion 1121F of the first housing 1120F and an arcuate button slot 1123R is formed at an upper end of the second grip portion 1121R of the second housing 1120R. If the reservoir module 1200 is assembled in the housing body 1100, the push button 1220 is movably positioned in the button slots 1123F and 1123R between the button protection arms 1112.

The reservoir module 1200 and the capillary tube module 1300 are disposed within the housing body 1100 along the central axis CA of the housing body 1100. The housing body 1100 includes an upper housing portion 1115U, which houses and fixes the reservoir module 1200, and a lower housing portion 1115L, which houses and fixes the capillary tube module 1300. The housing body 1100 has, on its inner surface, protrusion portions for fixing and supporting the reservoir module 1200. In this embodiment, by way of example of the protrusion portions for the reservoir module, the first housing 1120F has, on its inner surface, a support rib 1125FL supporting a lower surface of the reservoir housing 1230, an insertion rib 1125FU inserted into a portion of the reservoir housing 1230, and an engagement rib 1126F with which an upper end of the reservoir housing 1230 is in contact. Further, by way of example of the protrusion portions for the reservoir module, the second housing 1120R has, on its inner surface, a support rib 1125RL supporting the lower surface of the reservoir housing 1230, an insertion rib 1125RU inserted into a portion of the reservoir housing 1230, and an engagement rib 1126R with which the upper end of the reservoir housing 1230 is in contact. The housing body 1100 has, on its internal side, protrusion portions for fixing and supporting the capillary tube module 1300. In this embodiment, by way of example of the protrusion portions for the capillary tube module, the first housing 1120F has, on its inner surface, contact ribs 1127FU and 1127FL in contact with front surfaces of first and second flow caps, respectively, of the capillary tube module 1300, and the second housing 1120R has, on its inner surface, a support rib 1128R in contact with rear surfaces of the first and second flow caps of the capillary tube module 1300.

Figure 6:
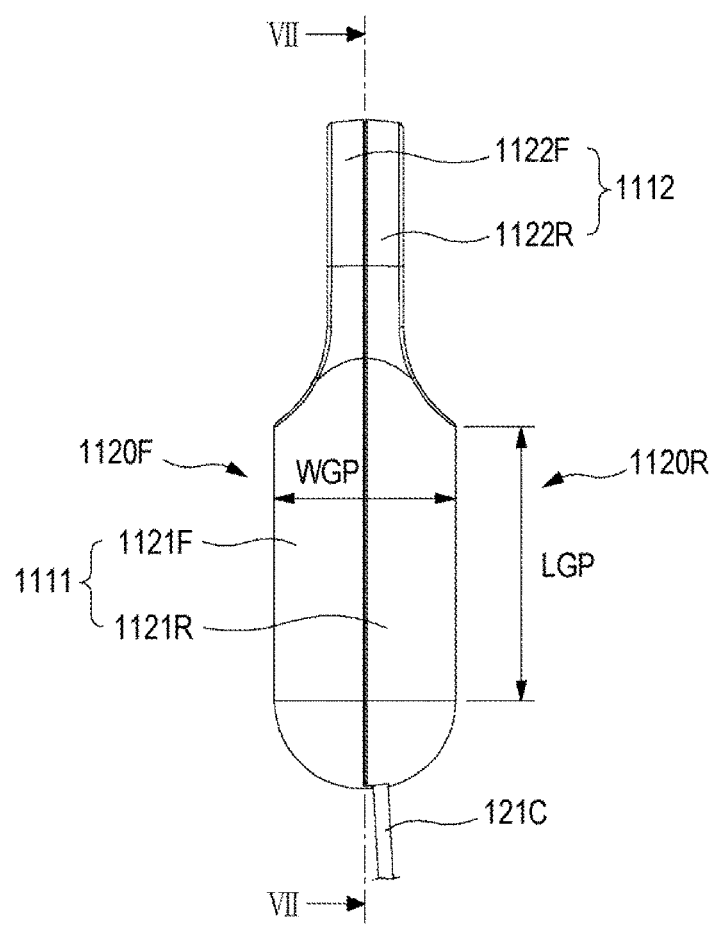
FIG. 6 is a side view of the medical fluid injector shown in FIG. 4.

As shown in FIG. 6, when the housing body 1100 is viewed from the side, the button protection arm 1112 has a width narrower than the width of the grip portion 1111. Thus, a transition surface 1116F, which transitions from the first grip portion 1121F to the first button protection arm 1122F, is formed at an outer surface of the first housing 1120F, and a transition surface 1116R, which transitions from the second grip portion 1121R to the second button protection arm 1122R, is formed at an outer surface of the second housing 1120R. Characters or numerals indicating information such as a name of a manufacturer, a one-time injection amount, etc. may be embossed or engraved in the transition surfaces 1116F and 1116R.

Among the tubes constituting the first supply path SP1 of the medical fluid supply device 100, the supply tube 121C and the discharge tube 121D, which are connected to the medical fluid injector 1000, are fitted to a lower edge of the housing body 1100. As shown in FIGS. 9 to 12, for fixing the supply tube 121C and the discharge tube 121D to the housing body 1100, a pair of U-shaped tube fixing recesses 1117R are formed at a lower edge of the second housing 1120R. Further, a pair of tube fixing protrusions 1117F, which are inserted to the tube fixing recesses 1117R, respectively, and fix the supply tube 121C and the discharge tube 121D to the respective tube fixing recesses 1117R, are formed at a lower edge of the first housing 1120F. The depths of the tube fixing recesses 1117R are greater than outer diameters of the supply tube 121C and the discharge tube 121D. Thus, when the capillary tube module 1300 is positioned in the second housing 1120R during assembly of the medical fluid injector 1000, the supply tube 121C and the discharge tube 121D can be stably retained in the tube fixing recesses 1117R. Further, the depths of the tube fixing recesses 1117R are deeper than protrusion lengths of the tube fixing protrusions 1117F, and the tube fixing protrusions 1117F have, at their tip ends, a curved surface corresponding to outer surfaces of the supply tube 121C and the discharge tube 121D. Accordingly, if the first housing 1120F and the second housing 1120R are assembled together, the supply tube 121C and the discharge tube 121D can be stably seated in the tube fixing recesses 1117R by the tube fixing protrusions 1117F.

The reservoir module 1200 of the medical fluid injector 1000 according to one embodiment is described in detail with reference to FIGS. 4 to 7 and 13 to 19.

The reservoir module 1200 is configured to temporarily store a predetermined amount of the medical fluid supplied from the medical fluid chamber 111 of the medical fluid supply device 100, and to discharge the stored medical fluid by pushing of the push button 1220. In this embodiment, the reservoir module 1200 includes the reservoir bag 1210 which stores the medical fluid supplied through the first supply path SP1 of the medical fluid supply device 100, the push button 1220 for pushing the reservoir bag 1210 to discharge the medical fluid in the reservoir bag 1210, and the reservoir housing 1230 which houses the reservoir bag 1210 and supports the push button 1220 such that the push button 1220 is movable along the central axis CA of the housing body 1100. Further, the reservoir module 1200 includes a support plate 1240, a pressing plate 1250 and a locker 1260. The support plate 1240 supports a lower surface of the reservoir bag 1210. The pressing plate 1250 is brought into surface contact with only a portion of an upper surface of the reservoir bag 1210 and presses the reservoir bag 1210 by pushing of the push button 1220. Along with the movement of the push button 1220, the locker 1260 opens and blocks a tube through which the medical fluid is supplied to the reservoir bag 1210 or a tube through which the medical fluid is discharged from the reservoir bag 1210.

The reservoir bag 1210 may be formed by high-frequency welding of two sheets 1210 U and 1210L, which are made of, for example, PVC, along edges of the two sheets. The reservoir bag 1210 has a storage portion 1211 which is approximately circular when viewed from above, an inlet flap 1212 formed at an edge of the storage portion 1211, and an outlet flap 1213 formed at an edge of the storage portion 1211 opposite the inlet flap 1212. The storage portion 1211 is expanded and contracted along the central axis CA of the housing body 1100 and stores the medical fluid in an inside portion 1211I. An inlet flow passage 1212FW extending from an end of the inlet flap 1212 to the inside portion 1211I of the storage portion 1211 is formed in an inside portion of the inlet flap 1212. An outlet flow passage 1213FW extending from an end of the outlet flap 1213 to the inside portion 1211I of the storage portion 1211 is formed in an inside portion of the outlet flap 1213. Further, the reservoir bag 1210 has an inlet tube 1214IT, which is connected to the inlet flow passage 1212FW of the inlet flap 1212, and an outlet tube 1214OT, which is connected to the outlet flow passage 1213FW of the outlet flap 1213. The inlet tube 1214IT is connected to an inlet tube port of the second flow cap of the capillary tube module 1300, and is thus fluidically connected to the supply tube 121C of the medical fluid supply device 100. The outlet tube 1214OT is connected to an outlet tube port of the second flow cap of the capillary tube module 1300, and is thus fluidically connected to the discharge tube 121D of the medical fluid supply device 100. Further, in this embodiment, a middle portion of the outlet tube 1214OT is pinched between the locker 1260 and a pressing plate provided on the lower surface of the reservoir housing 1230. The reservoir bag 1210 is located on a bottom portion 1231B of the reservoir housing 1230 with a support plate 1240 interposed between the bottom portion 1231B and the reservoir bag 1210.

The reservoir housing 1230 includes a cylindrical body which has a central axis coaxial or parallel with the central axis CA of the housing body 1100, and has a cylindrical housing portion in the cylindrical body. An upper end of the reservoir housing 1230 is open, while a lower end of the reservoir housing 1230 is closed. The reservoir housing 1230 has a circular bottom portion 1231B and a cylindrical side wall 1231SW extending along an edge of the bottom portion 1231B. A hook-shaped button stopper 1232 with which a portion of the push button 1220 is engaged is formed at an upper end of the side wall 1231SW of the reservoir housing 1230. The button stopper 1232 restricts the movement of the push button 1220 toward the button protection arms 1112, and prevents the push button 1220 from being separated upwardly from the reservoir housing 1230. Since both lateral portions of the button stopper 1232 are separated from the upper end of the side wall 1231SW, the button stopper 1232 can elastically deform toward the inside and outside of the reservoir housing 1230. The reservoir housing 1230 includes an insertion slot 1233, which is located adjacent to the bottom portion 1231B and extends in a circumferential direction of the reservoir housing 1230, and openings 1234L and 1234R located at both ends of the insertion slot 1233, respectively. The insertion slot 1233 and the openings 1234L and 1234R are formed to penetrate through the side wall 1231SW. The insertion slot 1233 extends at an angle greater than or equal to 180 degrees with respect to the central axis of the reservoir housing 1230 (or the central axis CA of the housing body 1100). The insertion slot 1233 has a width greater than a thickness of the sum of a thickness of the support plate 1240 and a thickness of the contracted reservoir bag 1210.

Since the reservoir housing 1230 is fixed in the inside of the housing body 1100, the reservoir module 1200 is assembled in the inside of the housing body 1100. The reservoir module 1200 is housed in the inside of the housing body 1100 in such a manner that the reservoir housing 1230 is positioned between the engagement rib 1126F and the support rib 1125FL of the first housing 1120F and between the engagement rib 1126R and the support rib 1125RL of the second housing 1120R, and that the insertion rib 1125FU of the first housing 1120F and the insertion rib 1125RU of the second housing 1120R are inserted into the insertion slot 1233 of the reservoir housing 1230. If the reservoir module 1200 is housed in the housing body 1100, the support ribs 1125FL and 1125RL support the lower surface of the bottom portion 1231B of the reservoir housing and the upper end of the side wall 1231SW of the reservoir housing can be in contact with the engagement rib 1126F and the engagement rib 1126R.

The support plate 1240 is disposed between the bottom portion 1231B of the reservoir housing 1230 and the lower surface of the reservoir bag 1210. The support plate 1240 is inserted to the inside of the reservoir housing 1230 through the insertion slot 1233. A boss 1241 protrudes from a center of the lower surface of the support plate 1240, and a hole corresponding to the boss 1241 is formed at a center of the upper surface of the bottom portion 1231B of the reservoir housing 1230. After the support plate 1240 is inserted in the reservoir housing 1230, the reservoir bag 1210 is inserted to the inside of the reservoir housing 1230 through the insertion slot 1233 and is located on the upper surface of the support plate 1240. If the reservoir bag 1210 is housed in the inside of the reservoir housing 1230, the inlet flap 1212 and the outlet flap 1213 protrude toward the outside of the reservoir housing 1230 through the respective openings 1234L and 1234R. Since the reservoir bag 1210 is housed in the inside of the reservoir housing 1230 through the insertion slot 1233, the reservoir bag 1210 with the inlet tube 1214IT and the outlet tube 1214OT attached thereto can be easily housed in the inside of the reservoir housing 1230. In another embodiment, the support plate 1240 may be integrally formed with the bottom portion 1231B of the reservoir housing 1230. In such an embodiment, the reservoir bag 1210 is located on the bottom portion of the reservoir housing 1230.

The pressing plate 1250 is disposed between the push button 1220 and the upper surface of the reservoir bag 1210. The pressing plate 1250 pushes the reservoir bag 1210 by pushing of the push button 1220 (a downward movement of the push button 1220 along the central axis CA). The pressing plate 1250 is inserted to the inside of the reservoir housing 1230 from the upper end of the reservoir housing 1230 to be located on the reservoir bag 1210. The pressing plate 1250 includes a cushion member 1251, which is in surface-contact with only a portion of the upper surface of the reservoir bag 1210, and a holder 1252 holding the cushion member 1251. The holder 1252 has a disk 1252P, which has a diameter approximately corresponding to an inner diameter of the side wall 1231SW, and a flange 1252F formed along an edge of the disk 1252P. The cushion member 1251 is fixed to the holder 1252 by tight fitting, and is made of, for example, a rubber material. The cushion member 1251 includes a disk-shaped fitting portion 1251F, which is fitted to the holder 1252, and a disk-shaped pressing portion 1251P, which protrudes downward from the fitting portion 1251F and is in surface-contact with a portion of the upper surface of the reservoir bag 1210. A diameter of the pressing portion 1251P of the cushion member 1251 is less than a diameter of the storage portion 1211 of the reservoir bag 1210.

The push button 1220 is coupled to the reservoir housing 1230 so as to be movable along the central axis CA of the housing body 1100. The push button 1220 includes a circular base portion 1221, which is fitted to the inside of the reservoir housing 1230, a button portion 1222 protruding upward from the base portion 1221, and a drive arm 1223, which extends downward from the base portion 1221 and drives the locker 1260. The base portion 1221 has a disk portion 1221P and a flange portion 1221F formed along an edge of the disk portion 1221P. A diameter of the disk portion 1221P is approximately the same as the diameter of the disk 1252P of the holder 1252. Stopper seats 1221S, which engage the button stoppers 1232 provided at the upper end of the reservoir housing 1230, are formed on an upper surface of the disk portion 1221P. The button portion 1222 protrudes upward from the upper surface of the disk portion 1221P of the base portion 1221, and has an approximate shape of a rectangular parallelepiped. A recess 1222R to which an insertion protrusion of the cotter 1400 is fitted is formed at a center of an upper surface of the button portion 1222. The drive arm 1223 extends downward from the flange portion 1221F of the base portion 1221 in parallel with the central axis CA of the housing body 1100 or in parallel with the central axis of the reservoir housing 1230.

The push button 1220 is vertically movable along the central axis CA of the housing body 1100 in the state where the base portion 1221 is housed in the reservoir housing 1230. To guide the vertical movement of the push button 1220, the reservoir housing 1230 includes a guide slot 1235, which extends in parallel with the central axis CA and is formed to penetrate through the side wall 1231SW of the reservoir housing 1230. Further, the reservoir housing 1230 includes a reinforcement lever 1236, which extends downward from a lower edge of the reservoir housing 1230 and a side surface of which is flush with a side surface of the guide slot 1235. When the drive arm 1223 drives the locker 1260, the side surface of the drive arm 1223 is brought into contact with the side surface of the reinforcement lever 1236, thereby preventing the drive arm 1223 from being bent. The push button 1220 is retained with respect to the reservoir housing 1230 in the state where the drive arm 1223 is slidably fitted to the guide slot 1235. The drive arm 1223 slides along a surface of the guide slot 1235. Since the guide slot 1235 extending in parallel with the central axis CA of the housing body 1100 restricts the drive arm 1223, the push button 1220 is movable only in the direction of the central axis CA of the housing body 1100. The push button 1220 includes a bias means for biasing the push button 1220 upward. In this embodiment, as the bias means of the push button 1220, the push button 1220 includes a button spring 1224, which is located within the base portion 1221 and is disposed between a lower surface of the base portion 1221 and an upper surface of the holder 1252. The button spring 1224 includes a compression coil spring, and is interposed between the base portion 1221 of the push button 1220 and an upper surface of the holder 1252 in the state where the button spring is compressed to a certain extent. Due to the restoring force of the button spring 1224, the push button 1220 is biased toward the button protection arms 1112 of the housing body 1100 or returns to its original position after the user pushes the push button.

In this embodiment, the capacity of the storage portion 1211 of the reservoir bag 1210 is determined to be about 1 cc. If the above-described cotter 1400 is removed from the medical fluid injector 1000, the storage portion 1211 of the reservoir bag 1210 is filled with the medical fluid, and at the same time, the storage portion 1211 is expanded in the direction of the central axis CA of the housing body 1100. The expansion of the storage portion 1211 moves the pressing plate 1250 and the push button 1220 toward the upper end of the housing body 1100. If the base portion 1221 of the push button 1220 is brought into contact with the button stopper 1232 provided at the upper end of the housing body 1100, the storage portion 1211 of the reservoir bag 1210 cannot expand further. At this time, the amount of the medical fluid stored in the storage portion 1211 becomes about 1 cc. As such, a length of the space, which allows the storage portion 12112 to expand along the central axis CA, is limited to a distance between an upper surface of the support plate 1240, which is located below the storage portion 1211, and a lower surface of the cushion member 1251, which is located below the push button 1220 in contact with the button stopper 1232. Accordingly, the control of the storage capacity of the storage portion 1211 can be performed precisely. That is, the storage capacity of the storage portion 1211 can be variously set by varying the position of the button stopper 1232 along the longitudinal direction of the housing body 1100. By way of another example, the storage capacity of the storage portion 1211 can be variously set by varying a thickness of the cushion member 1251 in the longitudinal direction of the housing body 1100.

The locker 1260 is located at the lower surface of the bottom portion 1231B of the reservoir housing 1230, and is coupled to the reservoir housing 1230 so as to be rotatable with respect to the central axis CA of the housing body 1100. The locker 1260 can open and block the inlet tube 1214IT or the outlet tube 1214OT of the reservoir bag 1210. In this embodiment, along with a downward movement of the push button 1220 (i.e., a movement of the push button 1220 in a direction in which the user pushes the push button 1220), the locker 1260 opens the outlet tube 1214OT, which extends from the reservoir bag 1210. And along with an upward movement of the push button 1220 (i.e., a movement of the push button 1220 caused by the restoring force of the button spring 1224), the locker 1260 blocks the outlet tube 1214OT of the reservoir bag 1210.

The locker 1260 includes a locking lever 1261, which is rotatably coupled to the reservoir housing 1230 so as to be rotated clockwise and counterclockwise with respect to the central axis CA of the housing body 1100, and a locker spring 1262, which biases the locking lever 1261 to press and block the outlet tube 1214OT of the reservoir bag 1210. The locking lever 1261 is rotated by the drive arm 1223 of the push button 1220. The locking lever 1261 has a shaft hole 1261H, a driven arm 1261DA which extends from the shaft hole 1261H and is in contact with the drive arm 1223 of the push button 1220, and a pressing arm 1261PA which extends from the shaft hole 1261H toward the opposite side of the driven arm 1261DA and presses the outlet tube 1214OT of the reservoir bag 1210. Further, a portion of the driven arm 1261DA, which is in contact with an end portion and a side portion of the drive arm 1223 of the push button 1220, comprises an inclined surface 1261IS, and the pressing arm 1261PA has a wedge-shaped pressing portion 1261PP which presses and blocks the outlet tube 1214OT of the reservoir bag 1210. The inclined surface 1261IS is inclined at about 20 degrees with respect to the central axis CA of the housing body 1100. Further, the locking lever 1261 has a spring holder 1261SH formed in the pressing arm 1261PA at the opposite side of the pressing portion 1261PP. Further, the locking lever 1261 has a reinforcement rib 1261RR, which is formed in the driven arm 1261DA at the opposite side of the inclined surface 1261IS and extends in a longitudinal direction of the driven arm 1261DA. Further, the locking lever 1261 has, on its upper and lower surfaces, a friction decreasing rib 1261FR which is formed in the driven arm 1261DA, and a friction decreasing rib 1261FR which is formed in the pressing arm 1261PA. If the reservoir module 1200 is housed in the housing body 1100, the locking lever 1261 can be in contact with the lower surface of the bottom portion 1231B of the reservoir housing 1230 and the upper surface of the support rib 1128R of the second housing 1120R through the respective friction decreasing ribs 1261FR. The locking lever 1261 of this embodiment has a linear shape, but the locking lever of other embodiments may have an L-like or V-like shape in which the driven arm 1261DA and the pressing arm 1261PA are bent at a certain angle.

To rotatably support the locking lever 1261, a rotation shaft 1231RS fitted to the shaft hole 1261H of the locking lever 1261 is formed on the lower surface of the bottom portion 1231B of the reservoir housing 1230. The rotation shaft 1231RS extends in the direction of the central axis CA of the housing body 1100 or in the direction of the central axis of the reservoir housing 1230. Further, for cooperation with the locking lever 1261, the reservoir housing 1230 has a pressing plate 1231PP, a tube holder 1231TH, and a spring holder 1231SH, which are formed on the lower surface of the bottom portion 1231B. The pressing plate 1231PP is located on the lower surface of the bottom portion 1231B opposite the pressing portion 1261PP of the locking lever 1261. The spring holder 1231SH of the reservoir housing 1230 is located on the lower surface of the bottom portion 1231B opposite the spring holder 1261SH of the locking lever 1261. The locker spring 1262 is coupled to the spring holder 1231SH of the reservoir housing 1230 and the spring holder 1261SH of the locking lever 1261 at both ends of the locker spring 1262. The locker spring 1262 includes a compression coil spring, and is disposed between the spring holder 1231SH of the reservoir housing 1230 and the spring holder 1261SH of the locking lever 1261 in the state where the locker spring 1262 is compressed to a certain extent. Thus, the locking lever 1261 is biased by the locker spring 1262 in a direction opposite to a direction in which the driven arm 1261DA is rotated by the drive arm 1223. That is, the locker spring 1262 applies a restoring force to the locking lever 1261 so as to bias the pressing portion 1261PP toward the pressing plate 1231PP.

In this embodiment, the rotation shaft 1231RS, the pressing plate 1231PP, the tube holder 1231TH, and the spring holder 1231SH, etc., which are used for fixing and blocking the outlet tube 1214OT, are integrally formed with the reservoir housing 1230. In another embodiment, the aforementioned parts, which are used for fixing and blocking the outlet tube 1214OT, may be formed as a single part that may be coupled to the bottom portion 1231B of the reservoir housing 1230. Further, in this embodiment, the rotation shaft 1231RS for rotation of the locking lever 1261 is formed at the center of the bottom portion 1231B of the reservoir housing 1230 so as to extend in the direction of the central axis CA of the housing body 1100. In another embodiment, the rotation shaft 1231RS may be formed at any location of the bottom portion 1231B in parallel with the central axis CA. Further, in another embodiment, the rotation shaft 1231RS for rotation of the locking lever 1261 may be formed at an inclined surface of the reservoir housing. In this case, an angle formed between the drive arm 1223 of the push button 1220 and the locking lever 1261 may be greater than or equal to 90 degrees.

Figure 18:
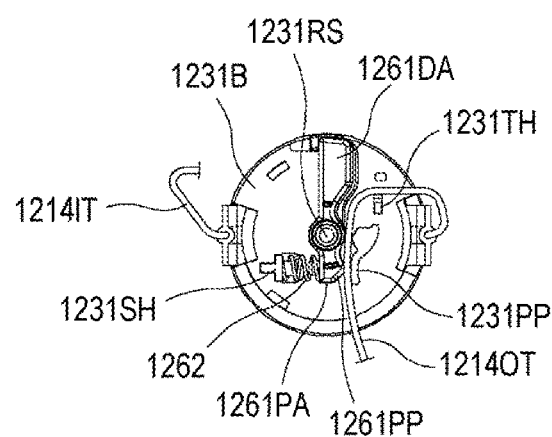
FIG. 18 is a bottom view of the reservoir module shown in FIG. 13.
Figure 19:
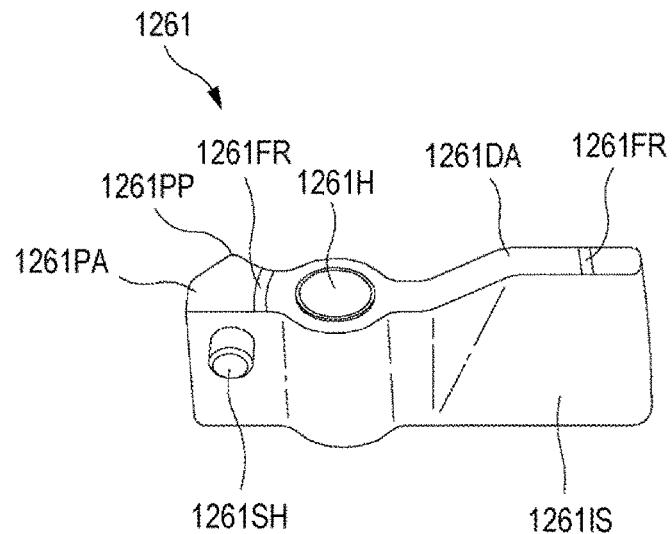
FIG. 19 is a perspective view showing a locking lever of a locker.
Figure 20:
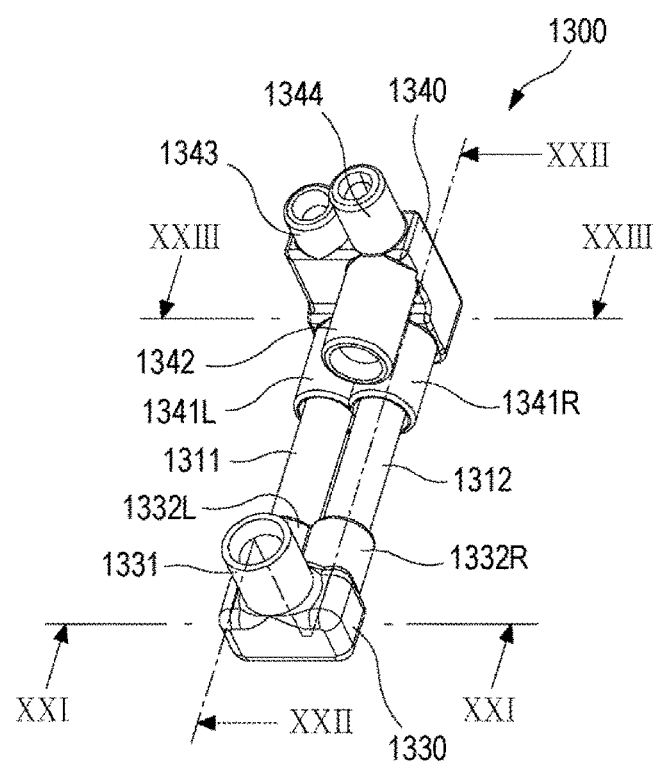
FIG. 20 is a perspective view of the capillary tube module shown in FIG. 13.

As shown in FIG. 18, a portion of the outlet tube 1214OT of the reservoir bag 1210 is fitted to the tube holder 1231TH, and another portion of the outlet tube 1214OT is interposed between the pressing portion 1261PP of the locking lever 1261 and the pressing plate 1231PP of the reservoir housing 1230. The locking lever 1261 is rotatable between a blocking position where the locking lever blocks the outlet tube 1214OT due to the restoring force of the locker spring 1262 and an opening position where the locking lever opens the outlet tube 1214OT along with a downward movement of the drive arm 1223 of the push button 1220. In the blocking position of the locking lever 1261, the drive arm 1223 is positioned above the inclined surface 1261IS of the locking lever 1261 and is not in contact with the inclined surface 1261IS. As the drive arm 1223 is brought into contact with the inclined surface 1261IS of the locking lever 1261 by the downward movement of the push button 1220 along the central axis CA, the locking lever 1261 is rotated due to the reaction from the force which the drive arm 1223 applies to the inclined surface 1261IS. Then, the pressing arm 1261PA, which is located at the opposite side of the driven arm 1261DA having the inclined surface 1261IS, is rotated away from the pressing plate 1231PP, thereby opening the outlet tube 1214OT. In contrast, if the push button 1220 is moved upward due to the restoring force of the button spring 1224, the pressing arm 1261PA is moved toward the pressing plate 1231PP due to the restoring force of the locker spring 1262, thereby blocking the outlet tube 1214OT.

The capillary tube module 1300 of the medical fluid injector 1000 according to one embodiment is described in detail with reference to FIGS. 4 to 7 and FIGS. 20 to 23.

A portion of the first supply path SP1 of the medical fluid supply device 100 is located in the capillary tube module 1300. Further, a portion of the second supply path SP2, which is used for the supply of the medical fluid to the reservoir bag 1210 and the discharge of the medical fluid from the reservoir bag 1210, is located in the capillary tube module 1300. The capillary tube module 1300 is disposed below the reservoir module 1200 within the housing body 1100 and is fixed to the housing body 1100.

In this embodiment, the capillary tube module 1300 includes a pair of first and second capillary tubes 1311 and 1312, a first medical fluid flow path 1321 extending through the first capillary tube 1311, and a second medical fluid flow path 1322 extending through the second capillary tube 1312. The first and second capillary tubes 1311 and 1312 are formed of, for example, a glass material. Each of the first and second capillary tubes 1311 and 1312 has a flow passage therein that is perforated in a longitudinal direction and has a diameter of about 0.001 mm to about 0.01 mm. The first medical fluid flow path 1321 is a flow path through which the medical fluid is supplied from the supply tube 121C of the medical fluid supply device 100 to the reservoir bag 1210. The second medical fluid flow path 1322 is a flow path through which the medical fluid flows from the supply tube 121C to the discharge tube 121D, and to which the medical fluid stored in the reservoir bag 1210 is added by pushing of the push button 1220. Further, the capillary tube module 1300 includes a first flow cap 1330 and a second flow cap 1340, which support the first and second capillary tubes 1311 and 1312 and form the first and second medical fluid flow paths 1321 and 1322.

Figure 13:
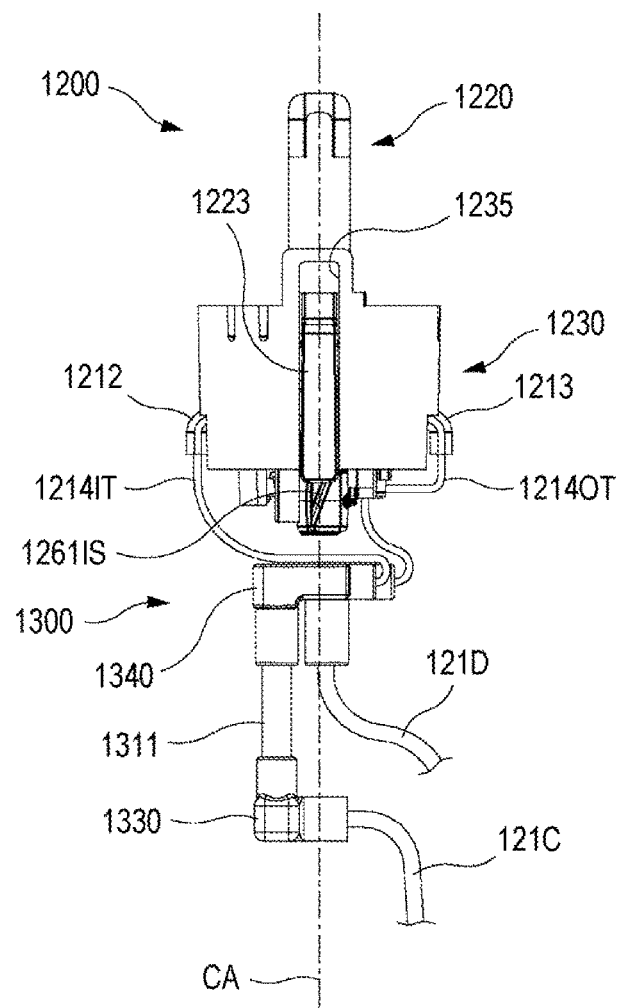
FIG. 13 is a side view showing a reservoir module and a capillary tube module of the medical fluid injector shown in FIG. 4.
Figure 14:
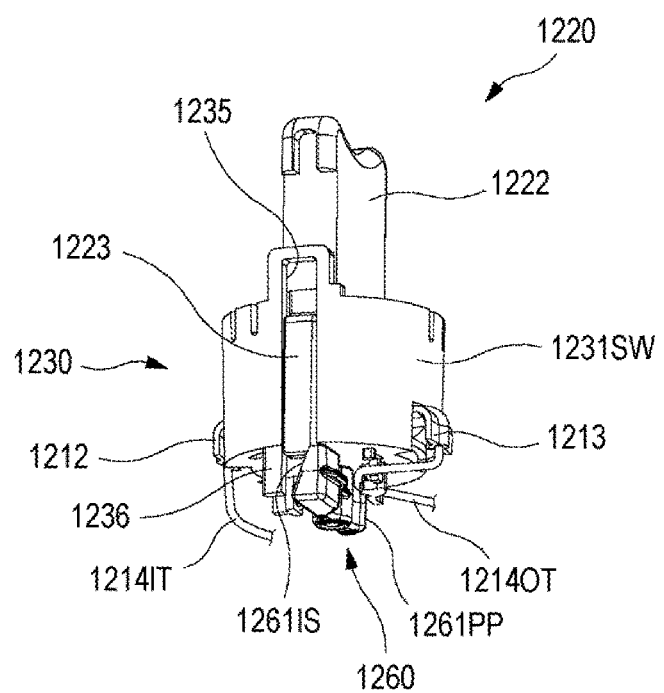
FIG. 14 is a lower perspective view of the reservoir module shown in FIG. 13.
Figure 15:
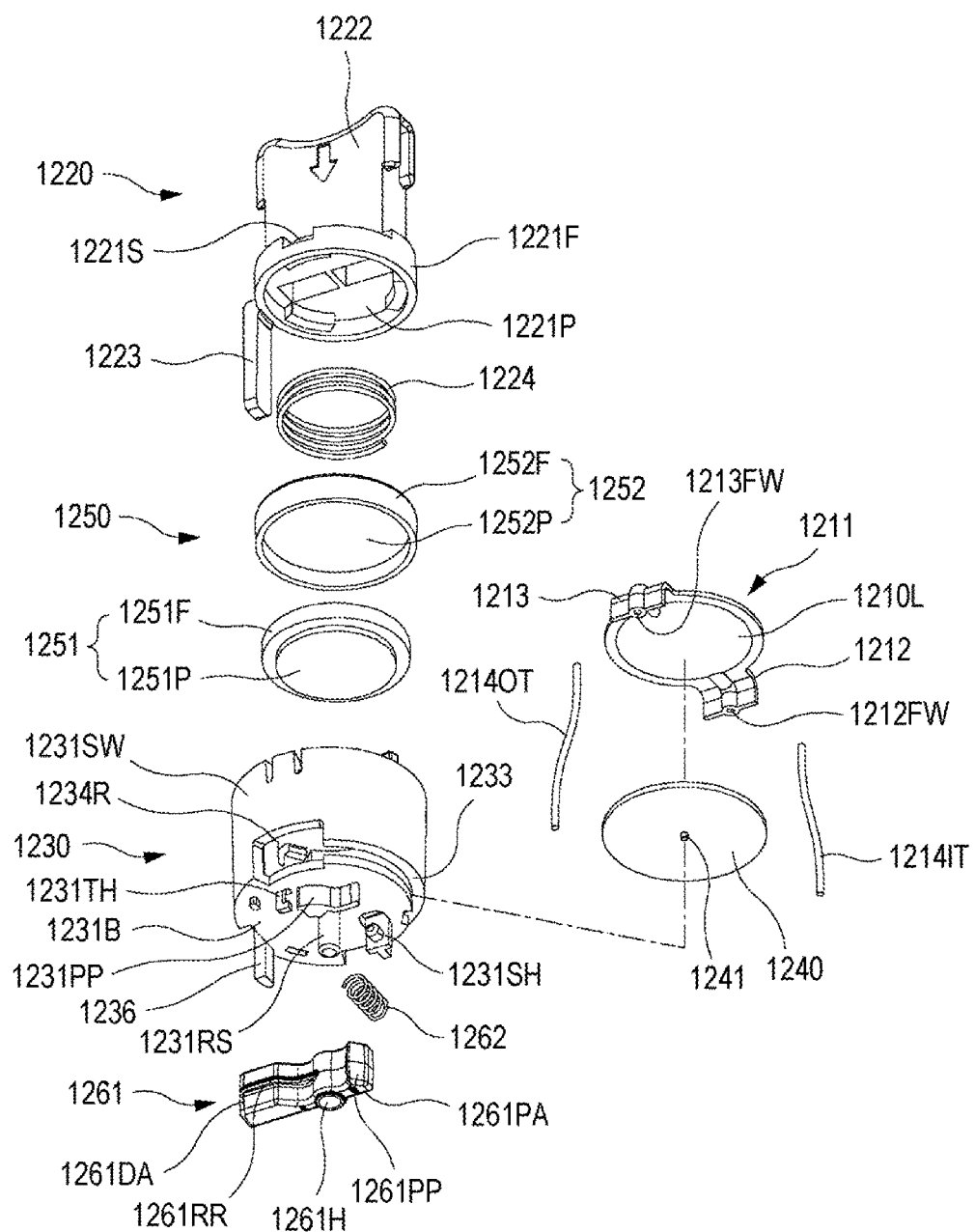
FIG. 15 is an exploded perspective view of the reservoir module shown in FIG. 13.
Figure 16:
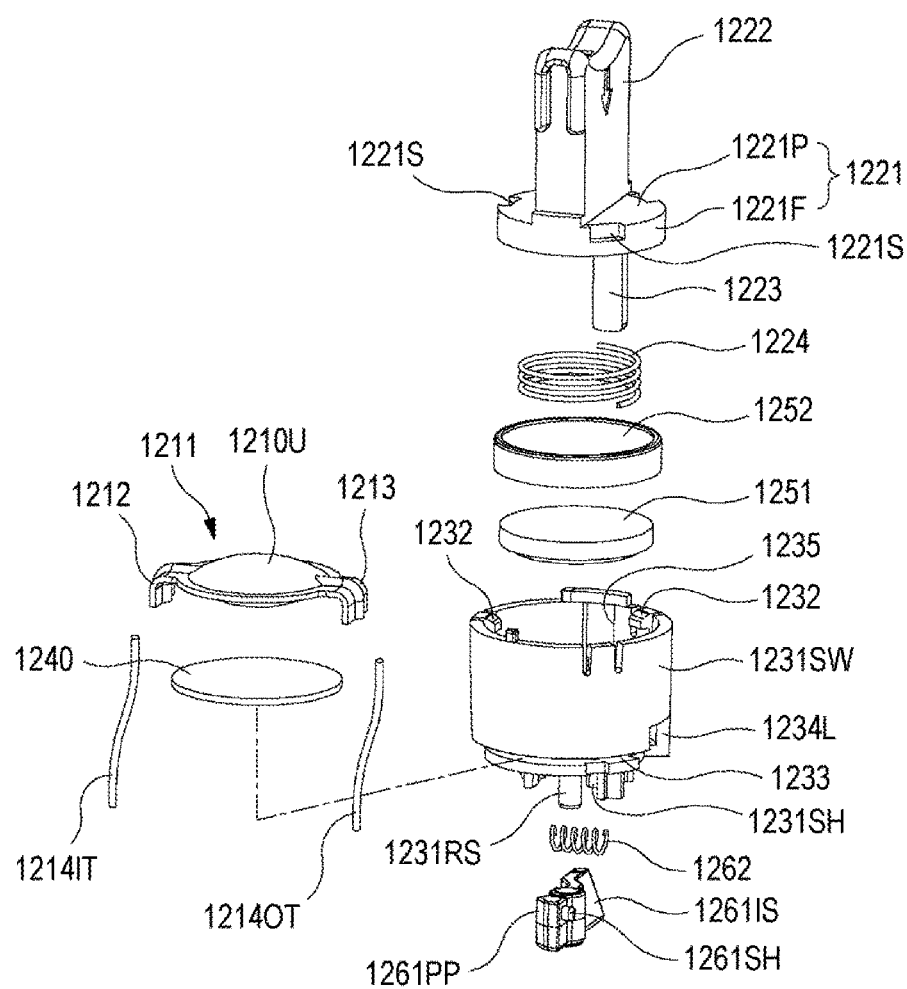
FIG. 16 is an exploded perspective view of the reservoir module shown in FIG. 13.
Figure 17:
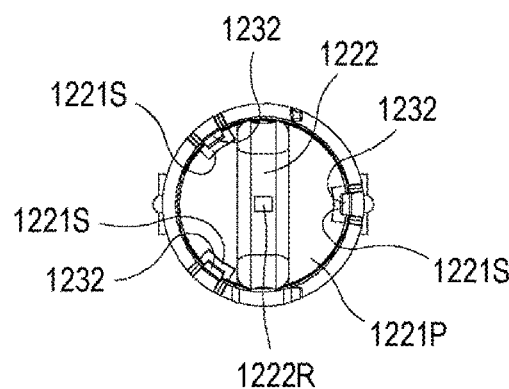
FIG. 17 is a top view of the reservoir module shown in FIG. 13.
Figure 21:
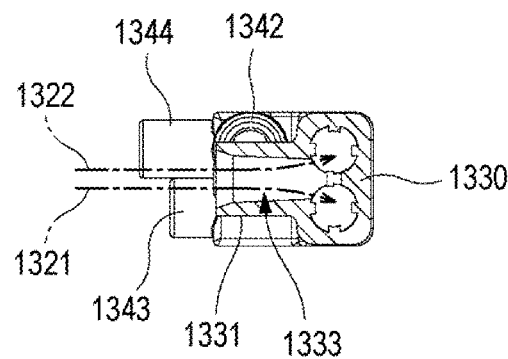
FIG. 21 is a sectional view taken along the line XXI-XXI of FIG. 20.

The first flow cap 1330 is located at a lower end of the capillary tube module 1300, and is connected to the supply tube 121C of the medical fluid supply device 100 (see FIG. 13). When viewed from the side, the first flow cap 1330 has an approximately L-like shape. The first flow cap 1330 includes a supply tube port 1331 to which the supply tube 121C of the medical fluid supply device 100 is connected, and a pair of capillary tube ports 1332L and 1332R to which the first and second capillary tubes 1311 and 1312, respectively, are connected. Further, as shown in FIG. 21, the first flow cap 1330 includes therein a medical fluid passage 1333 which extends from the supply tube port 1331 to the capillary tube ports 1332L and 1332R and is bifurcated midway. The first medical fluid flow path 1321 and the second medical fluid flow path 1322 pass the medical fluid passage 1333 of the first flow cap 1330.

Figure 22:
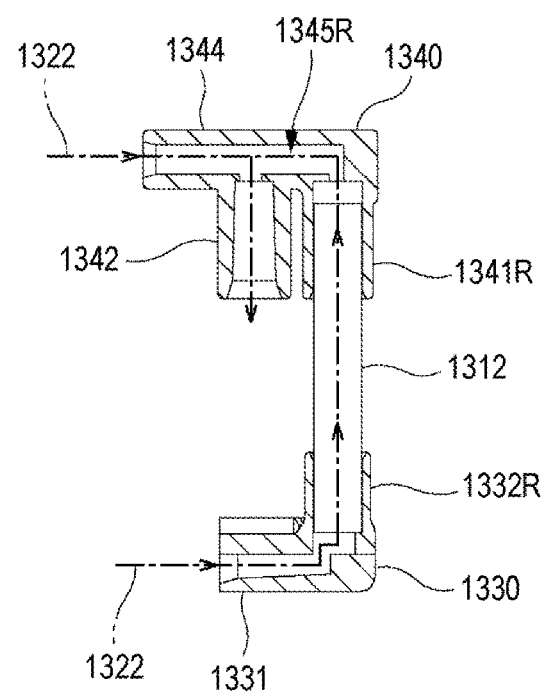
FIG. 22 is a sectional view taken along the line XXII-XXII of FIG. 20.
Figure 23:
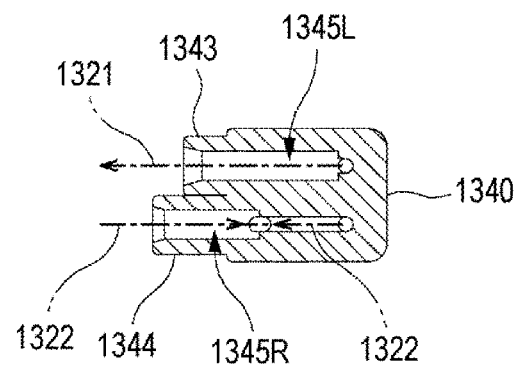
FIG. 23 is a sectional view taken along the line XXIII-XXIII of FIG. 20.

The second flow cap 1340 is located at an upper end of the capillary tube module 1300, and is connected to the discharge tube 121D of the medical fluid supply device 100 and the inlet tube 1214IT and the outlet tube 1214OT of the reservoir bag 1210 (see FIG. 13). When viewed from the side, the second flow cap 1340 has an approximately U-like shape. The second flow cap 1340 includes a pair of capillary tube ports 1341L and 1341R to which the first and second capillary tubes 1311 and 1312, respectively, are connected, a discharge tube port 1342 to which the discharge tube 121D of the medical fluid supply device 100 is connected, an inlet tube port 1343 to which the inlet tube 1214IT of the reservoir bag 1210 is connected, and an outlet tube port 1344 to which the outlet tube 1214OT of the reservoir bag 1210 is connected. Further, as shown in FIGS. 22 and 23, the second flow cap 1340 includes therein medical fluid passages 1345L and 1345R through which the medical fluid flows. The medical fluid passage 1345L of the second flow cap 1340 extends from the capillary tube port 1341L to the inlet tube port 1343. The medical fluid passage 1345R of the second flow cap 1340 extends from the capillary tube port 1341R to the discharge tube port 1342 and the outlet tube port 1344. As shown in FIG. 22, the medical fluid passage 1345R is divided into the discharge tube port 1342 and the outlet tube port 1344. Thus, when the push button 1220 of the medical fluid injector 1000 is not pushed, the medical fluid from the medical fluid chamber 111 of the medical fluid supply device 100 flows through the supply tube port 1331 and the capillary tube port 1332R of the first flow cap 1330, the second capillary tube 1312, the capillary tube port 1341R of the second flow cap 1340, the medical fluid passage 1345R, and the discharge tube port 1342. That is, when the push button 1220 of the medical fluid injector 1000 is not pushed, the medical fluid flows through the second medical fluid flow path 1322. However, if the user pushes the push button 1220 of the medical fluid injector 1000, additional medical fluid from the reservoir bag 1210 flows to the second flow cap 1340 through the outlet tube port 1344, and enters the discharge tube 121D of the medical fluid supply device 100 through the discharge tube port 1342 together with the medical fluid from the medical fluid chamber 111 of the medical fluid supply device 100 through the second capillary tube 1312.

The medical fluid injector 1000 includes the cotter 1400 for maintaining the medical fluid injector 1000 in the unused state. The cotter 1400 is removably positioned in the button protection arms 1112 such that the cotter presses the push button 1220 to contract the reservoir bag 1210 to a minimum. Such a cotter may be removed from the button protection arms 1112 through fracture. Alternatively, such a cotter may be removed from the button protection arms 1112 by pulling the cotter, which is fitted to the button protection arms 1112, from the button protection arms 1112.

Figure 24:
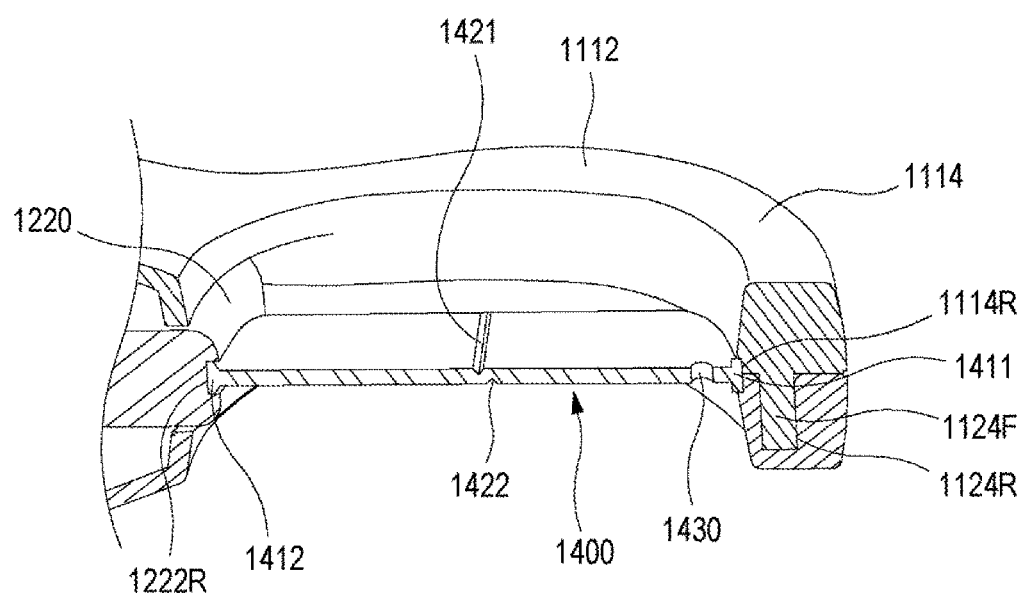
FIG. 24 is a perspective view showing an upper portion of the medical fluid injector shown in FIG. 3 together with a longitudinal section thereof.

The cotter 1400 shown in FIGS. 3 and 24 can be fractured and is removably fixed between the inner surface of the button protection arm 1112 and the upper surface of the push button 1220. Referring to FIGS. 3 and 24, the cotter 1400 has a shape of an approximately rectangular plate, and has an insertion protrusion 1411 at the middle of its upper end and an insertion protrusion 1412 at the middle of its lower end. The insertion protrusion 1411 located at the middle of the upper end is inserted into a recess 1114R formed at an upper inner surface of the connection portion 1114, and the insertion protrusion 1412 located at the middle of the lower end is inserted into the recess 1222R formed at the upper surface of the button portion 1222 of the push button 1220. Further, the cotter 1400 includes V-shaped grooves 1421 and 1422, which extend traversally in the middle of the respective front and rear surfaces and are for the purpose of fracture. If the user exerts a force on any one of the V-shaped grooves 1421 and 1422 by means of a finger or a suitable tool, the cotter 1400 can be fractured from the V-shaped grooves 1421 and 1422. Further, when the cotter 1400 is viewed from the side, the V-shaped groove 1421 of the front surface and the V-shaped groove 1422 of the rear surface are spaced apart from each other. A mark for informing the user of a direction, such as characters "PUSH", may be embossed or engraved on the front and rear surfaces of the cotter 1400. Further, the cotter 1400 has a through hole 1430 below the insertion protrusion 1411 located at the middle of the upper end. A tag, which includes information related to the use of the medical fluid injector or the cotter, may be affixed to the through hole 1430.

Figure 25:
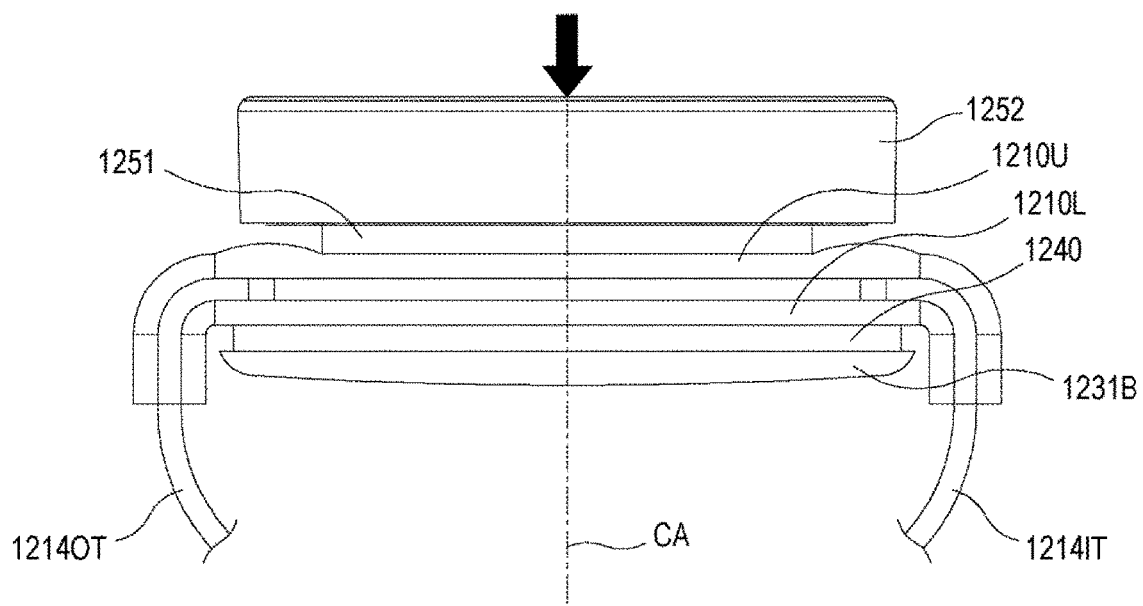
FIG. 25 is a side view schematically showing that a reservoir bag is contracted to a minimum by a cotter.

If the cotter 1400 is fixed between the button protection arm 1112 and the push button 1220, the reservoir bag 1210 is contracted to the minimum in the direction of the central axis CA of the housing body 1100 due to pushing of the push button 1220. That is, the shape and dimension of the cotter 1400 is determined so as to contract the reservoir bag 1210 to the minimum in the direction of the central axis CA of the housing body 1100. Accordingly, as shown in FIG. 25, if the cotter 1400 is fixed between the button protection arm 1112 and the push button 1220, the reservoir bag 1210 is fully compressed by the cushion member 1251 and the upper sheet 1210U and the lower sheet 1210L of the reservoir bag 1210 are brought into contact with each other. However, since the diameter of the storage portion 1211 of the reservoir bag 1210 is greater than the diameter of the cushion member 1251, a portion, at which the upper sheet 1210U and the lower sheet 1210L are not in contact with each other, is formed in the storage portion 1211 of the reservoir bag 1210 in a shape of a ring along a circumferential direction of the cushion member 1251. The medical fluid injector 1000 in the unused state, in which the reservoir module 1200 and the capillary tube module 1300 are disposed and the cotter 1400 is disposed between the push button 1220 and the button protection arm 1112, is connected to the medical fluid supply device 100. Before using the medical fluid supply device 100 on a patient, a priming operation must be performed to discharge air in the tubes of the medical fluid supply device 100 and air in the reservoir bag 1210 and the tubes of the medical fluid injector 1000. If the medical fluid is allowed to flow from the medical fluid chamber 111 of the medical fluid supply device 100 toward the connector 125, the medical fluid flows through various tubes located within the medical fluid injector 1000, and the priming operation is performed within the medical fluid injector 1000 accordingly. In particular, in the state where the push button 1220 is pushed by the cotter 1400 for the minimum contraction, a ring-shaped space is formed in the storage portion 1211 of the reservoir bag 1210 by the cushion member 1251 along the circumference of the cushion member 1251. Accordingly, when the medical fluid passes through the reservoir bag 1210 for the priming operation, most of the storage portion 1211 of the reservoir bag 1210 is blocked and the medical fluid passes through the storage portion 1211 only through the aforementioned ring-shaped space. Thus, the priming operation on the reservoir bag 1210 is performed in a highly reliable manner. After the priming operation is completed, the medical fluid injector 1000 comes to be in the useable state by removing the cotter 1400.

If the cotter 1400 is removed, the storage portion 1211 of the reservoir bag 1210 is filled with the medical fluid. Further, as the reservoir bag 1210 expands in the direction of the central axis CA of the housing body 1100, the reservoir bag 1210 pushes the pressing plate 1250 and the push button 1220 upwardly of the housing body 1100. If the base portion 1221 of the push button 1220 comes in contact with the button stopper 1232 located at the upper end of the reservoir housing 1230, the expansion of the reservoir bag 1210 caused by injection of the medical fluid is completed.

Figure 26:
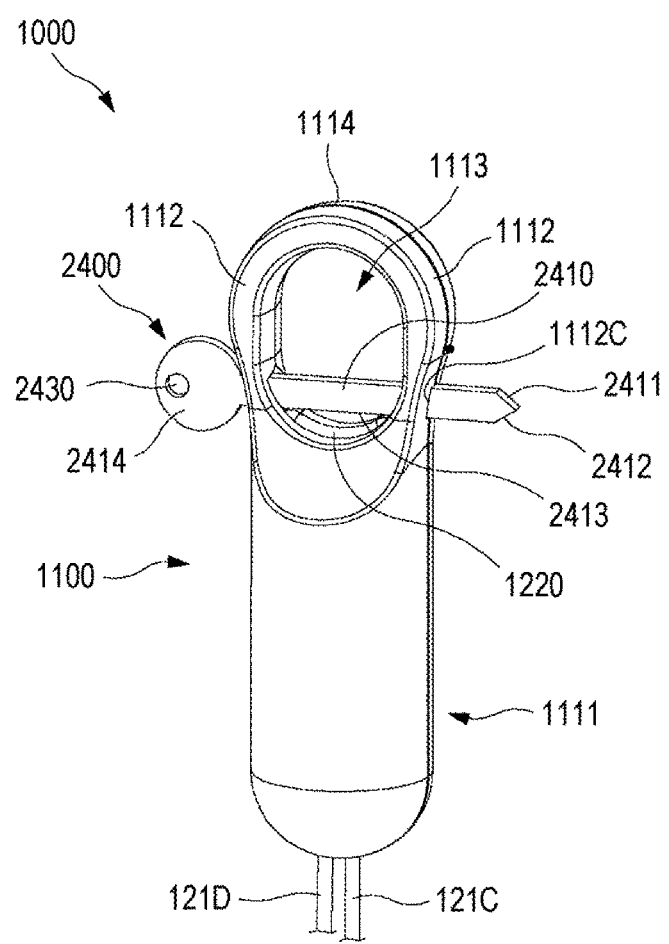
FIG. 26 is a perspective view of a medical fluid injector, showing another example of a cotter.

The cotter according to another example may be fixed to the button protection arm 1112 through fitting such that the reservoir bag 1210 can contract to the minimum upon pushing of the push button 1220, and may be removed from the button protection arm 1112 by being pulled from the button protection arm. An example of such a cotter is shown in FIG. 26. A cotter 2400 shown in FIG. 26 has a shape of a key. The cotter 2400 can be fitted to the button protection arm 1112 in a direction orthogonal to the longitudinal direction of the grip portion 1111, and can be removed by being pulled out in the direction orthogonal to the longitudinal direction of the grip portion 1111.

The cotter 2400 includes a pin body 2410 having a length longer than the width of the grip portion 1111. Each of the button protection arms 1112 is formed with a cotter hole 1112C through which the pin body 2410 passes through fitting. The pin body 2410 of the cotter 2400 has a pointed end. The pin body 2410 has a pair of inclined surfaces 2411 and 2412 at such an end. The pin body 2410 pushes the push button 1220 at its side surface 2413. Further, the pin body 2410 has a circular-shaped opposite end 2414 that can be held by fingers. The opposite end 2414 is formed with a through hole 2430. A tag, which includes information related to the use of the medical fluid injector or the cotter, may be affixed to the through hole 2430.

As the pin body 2410 of the cotter 2400 is fitted to the button protection arms 1112 through the cotter holes 1112C in the direction orthogonal to the longitudinal direction of the grip portion 1111, the pin body 2410 pushes the push button 1220 to contract the reservoir bag 1210 to the minimum. Similar to the above-described operation of the cotter 1400, if the cotter 2400 is removed from the button protection arms 1112 by pulling the pin body 2410 from the button protection arms 1112, the reservoir bag 1210 is filled with the medical fluid and the medical fluid injector 1000 comes to be in the useable state.

The medical fluid injector 1000 of the above-described embodiment includes the reservoir module 1200 and the capillary tube module 1300, which are fixed to the housing body 1100. The medical fluid injector of another embodiment may include only the reservoir module 1200 within the housing body 1100. In such an embodiment, the capillary tube module may be located outside the housing body 1100 and may be fluidically connected to the supply tube 121C and the discharge tube 121D of the medical fluid supply device 100. Further, the reservoir bag 1210 of the reservoir module 1200 may be connected to the capillary tube module via two tubes.

The width of the button protection arm 1112 in the medical fluid injector 1000 of the above-described embodiment is less than the width of the grip portion 1111. The medical fluid injector of another embodiment may include the button protection arm having a width equal to or greater than the width of the grip portion 1111.

Figure 27:
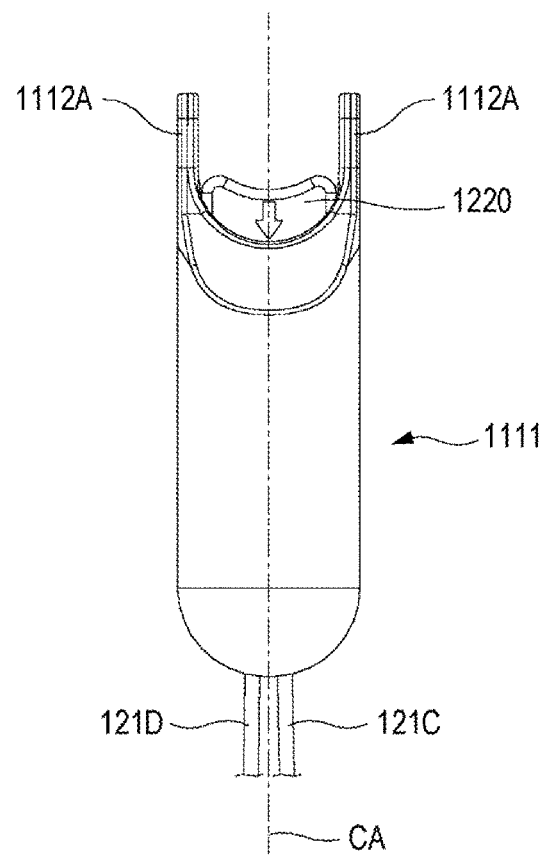
FIG. 27 is a front view of a medical fluid injector, showing another example of a button protection arm.

Further, the button protection arms 1112 of the medical fluid injector 1000 of the above-described embodiment are curved upwardly with a slight curvature from the upper end of the grip portion 1111 and are integrally formed through the connection portion 1114. Thus, when the medical fluid injector 1000 is viewed from the front, the button protection arms 1112 form an approximately annular shape. As shown in FIG. 27, the medical fluid injector of another embodiment may not include the above-described connection portion 1114. Further, as shown in FIG. 27, the button protection arms 1112A may extend in a nearly straight line from the upper end of the grip portion 1111. In the embodiment illustrated in FIG. 27, the cotter for pushing the push button 1220 may be removably fixed to only the button protection arms 1112A.

Figure 28:
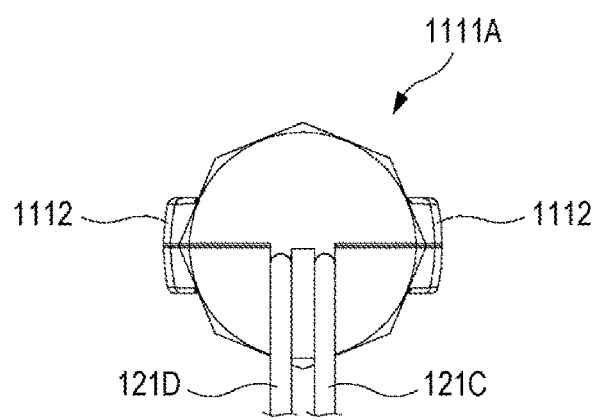
FIG. 28 is a bottom view of a medical fluid injector, showing another example of a grip portion.
Figure 29:
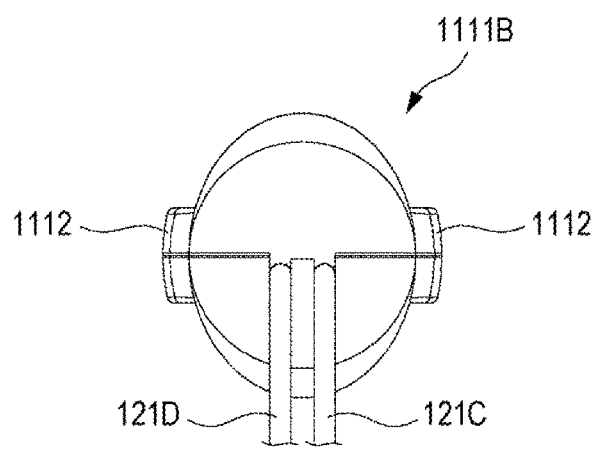
FIG. 29 is a bottom view of a medical fluid injector, showing a further example of a grip portion.

The grip portion 1111 of the medical fluid injector 1000 of the above-described embodiment has a cylindrical shape extending in the longitudinal direction of the housing body 1100. The grip portion of the medical fluid injector of another embodiment may have a shape of a polygonal cylinder extending in the longitudinal direction of the housing body 1100. By way of example, as shown in FIG. 28, the grip portion 1111A may have a shape of an octagonal cylinder. The example of the polygonal cylindrical grip portion is not limited to FIG. 28, and the grip portion may have a shape of a polygonal cylinder having an outer cross-sectional peripheral shape of a polygon of at least a triangle. Further, as shown in FIG. 29, the grip portion 1111B of the medical fluid injector of yet another embodiment may have a shape of an elliptical cylinder. As such, the grip portion of the medical fluid injector according to the embodiments may have a shape of a cylinder, an elliptical cylinder, or a polygonal cylinder. Thus, the cross-sectional shape of the grip portion of the housing body 1100 may include any one of a circle, an ellipse, and a polygon of at least a triangle.

The present disclosure described heretofore should not be limited to the above-described embodiments and the accompanying drawings. It will be apparent to those of ordinary skill in the technical field to which the present disclosure pertains, that various substitutions, modifications and alternations may be made without departing from the technical idea of the present disclosure.

DESCRIPTION OF REFERENCE SYMBOLS

100 medical fluid supply device, 110 chamber assembly, 111 medical fluid chamber, 112 gas generator, 113 plug, 114 plunger, 120 tube assembly, 121A, 121B tube, 121C supply tube, 121D discharge tube, 122 valve device, 123 clamp, 124 filter, 125 connector, 1000 medical fluid injector, 1100 housing body, 1111, 1111A, 1111B grip portion, 1112, 1112A button protection arm, 1112C cotter hole, 1113 insertion opening, 1114 connection portion, 1114R recess, 1115U upper housing portion, 1115L lower housing portion, 1116F transition surface, 1116R transition surface, 1117F tube fixing protrusion, 1117R tube fixing recess, 1120F first housing, 1120R second housing, 1121F first grip portion, 1121R second grip portion, 1122F first button protection arm, 1122R second button protection arm, 1123F button slot, 1123R button slot, 1124F dowel, 1124R dowel hole, 1125FU, 1125RU insertion rib, 1125FL, 1125RL support rib, 1126F, 1126R engagement rib, 1127FU, 1127FL contact rib, 1128R support rib, 1200 reservoir module, 1210 reservoir bag, 1210U, 1210L sheet of reservoir bag, 1211 storage portion, 1211I inside portion of storage portion, 1212 inlet flap, 1212FW inlet flow passage, 1213 outlet flap, 1213FW outlet flow passage, 1214IT inlet tube, 1214OT outlet tube, 1220 push button, 1221 base portion, 1221P disk portion of base portion, 1221F flange portion of base portion, 1221S stopper seat, 1222 button portion, 1222R recess, 1223 drive arm, 1224 button spring, 1230 reservoir housing, 1231B bottom portion, 1231SW side wall portion, 1231RS rotation shaft, 1231PP pressing plate, 1231TH tube holder, 1231SH spring holder, 1232 button stopper, 1233 insertion slot, 1234L, 1234R opening, 1235 guide slot, 1236 reinforcement lever, 1240 support plate, 1241 boss, 1250 pressing plate, 1251 cushion member, 1251F fitting portion, 1251P pressing portion, 1252 holder, 1252P disk of holder, 1252F flange of holder, 1260 locker, 1261 locking lever, 1261H shaft hole, 1261DA driven arm, 1261PA pressing arm, 1261IS inclined surface, 1261PP pressing portion, 1261SH spring holder, 1261RR reinforcement rib, 1261FR friction decreasing rib, 1262 locker spring, 1300 capillary tube module, 1311 first capillary tube, 1312 second capillary tube, 1321 first medical fluid flow path, 1322 second medical fluid flow path, 1330 first flow cap, 1331 supply tube port, 1332L, 1332R capillary tube port, 1333 medical fluid passage of first flow cap, 1340 second flow cap, 1341L, 1341R capillary tube port, 1342 discharge tube port, 1343 inlet tube port, 1344 outlet tube port, 1345L, 1345R medical fluid passage of second flow cap, 1400 cotter, 1411, 1412 insertion protrusion, 1421, 1422 V-shaped groove, 1430 through hole, 2400 cotter, 2410 pin body, 2411, 2412 inclined surface, 2413 side surface, SP1 first supply path of medical fluid, SP2 second supply path of medical fluid, CA central axis of housing body, LGP length of grip portion in longitudinal direction of housing body, WGP width of grip portion in direction orthogonal to longitudinal direction of housing body.

What is claimed is:

1. A medical fluid injector connected to a supply tube through which medical fluid is supplied and a discharge tube through which the medical fluid is discharged, and configured to store and discharge the medical fluid, the medical fluid injector comprising:
   a housing body having a central axis extending in a longitudinal direction, the housing body including:
      a grip portion forming a portion of an outer peripheral surface of the housing body, a length of the grip portion in the longitudinal direction being greater than a width of the grip portion in a direction orthogonal to the longitudinal direction; and
      a pair of button protection arms located at one end of the housing body along the central axis of the housing body, the button protection arms being adjacent to the grip portion;
   a reservoir module fixed within the housing body, the reservoir module including:
      a reservoir bag fluidically connected to the supply tube and the discharge tube and configured to store the medical fluid;
      a push button partially positioned between the button protection arms and movable along the central axis, the push button being configured to push the reservoir bag to discharge the medical fluid in the reservoir bag; and
      a pressing plate disposed between the reservoir bag and the push button and configured to press the reservoir bag by pushing of the push button, the pressing plate including a cushion member in surface-contact with a portion of an upper surface of the reservoir bag; and
   a cotter removably fixed between the button protection arms and the push button so as to push the push button,
   wherein, when the push button is pushed by the cotter, the cushion member pushes the reservoir bag to contract the reservoir bag to a minimum in the direction of the central axis.

2. The medical fluid injector of claim 1, wherein the reservoir bag includes an inlet tube fluidically connected to the supply tube and an outlet tube fluidically connected to the discharge tube,
   wherein the reservoir module further includes:
   a reservoir housing configured to house the reservoir bag and to support the push button such that the push button is movable along the central axis; and
   a locker configured to open and block one of the inlet tube and the outlet tube of the reservoir bag along with a movement of the push button.

3. The medical fluid injector of claim 2, wherein the locker includes:
   a locking lever rotatably coupled to the reservoir housing and configured to press the one of the inlet tube and the outlet tube; and
   a locker spring configured to bias the locking lever such that the locking lever presses the one of the inlet tube and the outlet tube.

4. The medical fluid injector of claim 3, wherein the push button includes a drive arm for rotating the locking lever,
   wherein the reservoir housing includes a guide slot to which the drive arm is slidably fitted, the guide slot extending in parallel with the central axis, wherein the locking lever includes a driven arm in contact with the drive arm and a pressing arm pressing the one of the inlet tube and the outlet tube, and wherein the locker spring biases the locking lever in a direction opposite to a direction in which the driven arm is rotated by the drive arm.

5. The medical fluid injector of claim 4, wherein a portion of the driven arm in contact with at least a side portion of the drive arm includes an inclined surface, and wherein the inclined surface is inclined with respect to the central axis.

6. The medical fluid injector of claim 2, wherein the reservoir housing includes:

a bottom portion on which the reservoir bag is placed;

a side wall extending along an edge of the bottom portion; and an insertion slot formed adjacent to the bottom to penetrate through the side wall, and wherein the reservoir bag is inserted inside of the reservoir housing through the insertion slot.

7. The medical fluid injector of claim 6, wherein the reservoir module further includes a support plate disposed between the bottom portion of the reservoir housing and a lower surface of the reservoir bag.

8. The medical fluid injector of claim 6, wherein, at an inner surface of the housing body, the housing body includes:

a support rib supporting a lower surface of the bottom portion of the reservoir housing;

an engagement rib in contact with an upper end of the side wall of the reservoir housing; and an insertion rib inserted into the insertion slot of the reservoir housing.

9. The medical fluid injector of claim 2, wherein the reservoir housing includes a button stopper restricting a movement of the push button toward the button protection arms.

10. The medical fluid injector of claim 9, wherein the button stopper is elastically deformable toward inside and outside of the reservoir housing.

11. The medical fluid injector of claim 1, wherein the push button includes a button spring disposed between a lower surface of the push button and the pressing plate and configured to bias the push button toward the button protection arms.

12. The medical fluid injector of claim 1, wherein the cotter is removably fitted to the button protection arms.

13. The medical fluid injector of claim 1, further comprising a capillary tube module fixed adjacent to the reservoir module within the housing body, wherein the capillary tube module includes:

a first capillary tube;

a first medical fluid flow path through which the medical fluid is supplied from the supply tube via the first capillary tube to the reservoir bag;

a second capillary tube; and a second medical fluid flow path through which the medical fluid flows from the supply tube via the second capillary tube to the discharge tube and through which the medical fluid stored in the reservoir bag is supplied.

14. The medical fluid injector of claim 1, wherein the pair of the button protection arms are integrally formed.

15. The medical fluid injector of claim 14, wherein the pair of the button protection arms form an annular shape.

16. The medical fluid injector of claim 1, wherein the housing body includes a first housing, which comprises a half portion of the housing body with respect to the central axis, and a second housing, which comprises another half portion of the housing body with respect to the central axis, wherein the first housing includes a pair of tube fixing protrusions at a lower edge, and wherein the second housing includes, at a lower edge, a pair of tube fixing recesses to which the tube fixing protrusions are inserted respectively and which are deeper than protrusion lengths of the tube fixing protrusions.

17. The medical fluid injector of claim 1, wherein a cross sectional shape of the grip portion of the housing body includes any one of a circle, an ellipse, and a polygon of at least a triangle.

18. A medical fluid supply device, comprising:

a chamber assembly having a medical fluid chamber configured to store medical fluid;

a tube assembly connecting the medical fluid chamber and a user; and the medical fluid injector of claim 1, wherein the tube assembly includes the supply tube through which the medical fluid is supplied from the medical fluid chamber to the medical fluid injector and the discharge tube through which the medical fluid is discharged from the medical fluid injector, and wherein the reservoir bag of the medical fluid injector is fluidically connected to the supply tube and the discharge tube.

* * * * *